(12) United States Patent
Thompson et al.

(10) Patent No.: US 7,926,944 B2
(45) Date of Patent: Apr. 19, 2011

(54) APPLICATION OF NEURO-OCULAR WAVEFRONT DATA IN VISION CORRECTION

(76) Inventors: Keith P. Thompson, Atlanta, GA (US); Jose R. Garcia, Mableton, GA (US); Phillip Randall Staver, Hagaman, NY (US)

( * ) Notice: Subject to any disclaimer, the term of this patent is extended or adjusted under 35 U.S.C. 154(b) by 0 days.

(21) Appl. No.: 12/799,503

(22) Filed: Apr. 26, 2010

(65) Prior Publication Data

US 2010/0231855 A1   Sep. 16, 2010

Related U.S. Application Data

(62) Division of application No. 10/811,368, filed on Mar. 26, 2004, now Pat. No. 7,703,919.

(60) Provisional application No. 60/458,480, filed on Mar. 28, 2003.

(51) Int. Cl.
*A61B 3/10* (2006.01)

(52) U.S. Cl. .......................... 351/205; 351/222; 351/246

(58) Field of Classification Search .................. 351/205, 351/222, 246
See application file for complete search history.

(56) References Cited

U.S. PATENT DOCUMENTS

| 5,258,791 | A | 11/1993 | Penney et al. |
|---|---|---|---|
| 5,480,396 | A | 1/1996 | Simon et al. |
| 5,599,340 | A | 2/1997 | Simon et al. |
| 5,777,719 | A | 7/1998 | Williams et al. |
| 6,000,800 | A | 12/1999 | Webb et al. |
| 6,095,651 | A | 8/2000 | Williams et al. |
| 6,099,125 | A | 8/2000 | Webb et al. |
| 6,499,843 | B1 | 12/2002 | Cox et al. |
| 6,511,180 | B2 | 1/2003 | Guirao et al. |
| 2003/0107814 | A1 | 6/2003 | Altmann |
| 2008/0106698 | A1* | 5/2008 | Dai et al. ........................ 351/246 |

OTHER PUBLICATIONS

Duane's Clinical Ophthalmology, Chapter 33, pp. 50-51, vol. 1.
McRae et al, "Customized Corneal Ablation the Quest for SuperVision", 2001, Chapter 5, pp. 52-54, Slack Incorporated, Thorofare, NJ.
Duane's Clinical Ophthalmology, Chapter 4, pp. 1-13, Chapter 5, pp. 1-8, vol. 2.

* cited by examiner

*Primary Examiner* — Huy K Mai
(74) *Attorney, Agent, or Firm* — Thomas, Kayden, Horstemeyer & Risley, LLP

(57) ABSTRACT

The present disclosure provides systems and methods for diagnosing and treating subjects using neuro-ocular wavefront data. As such, in some embodiments, among others, neuro-ocular wavefront data is obtained, and one or more characteristics of a visual system are ascertained from the neuro-ocular wavefront data.

58 Claims, 34 Drawing Sheets

FIG. 13

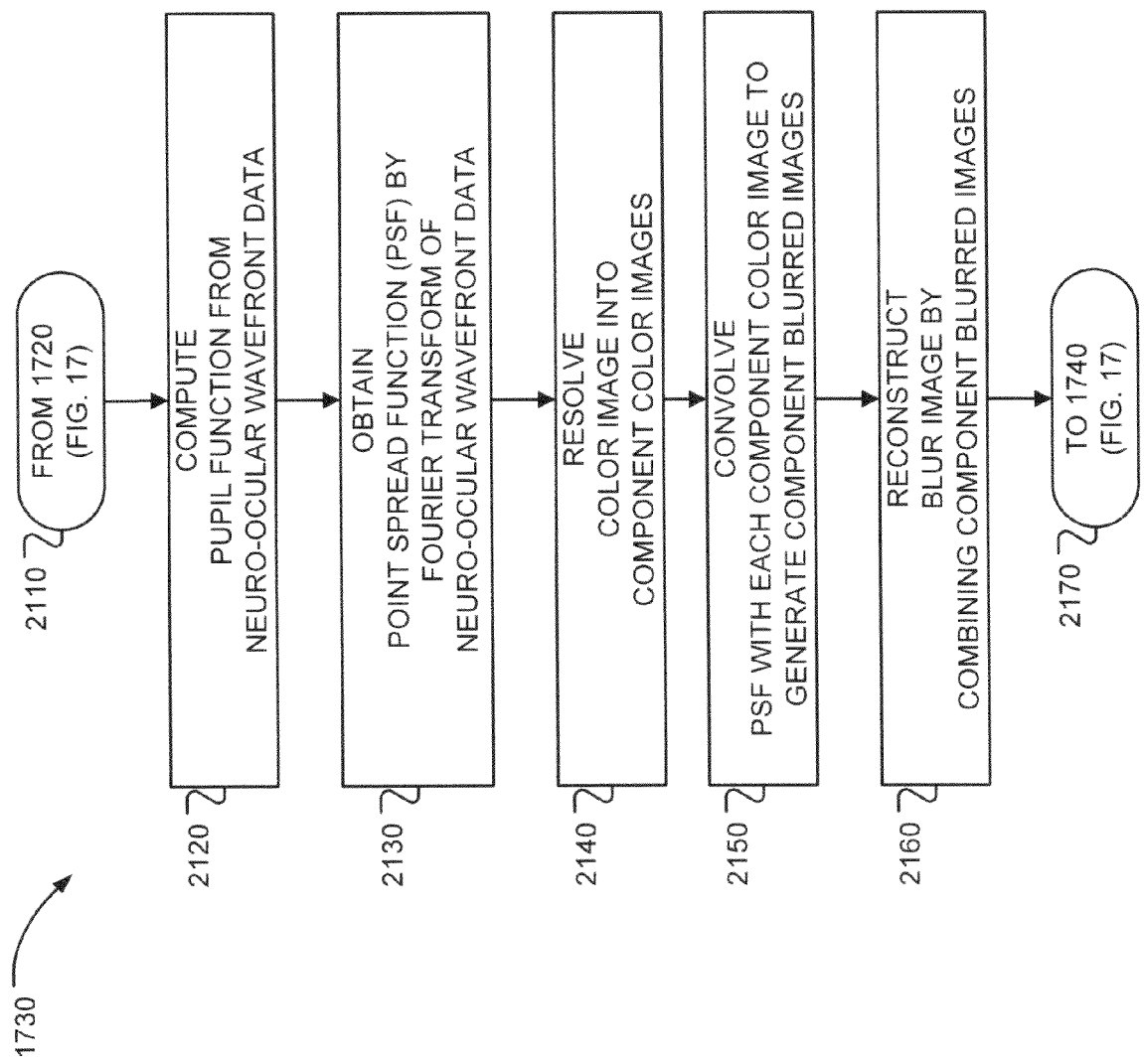

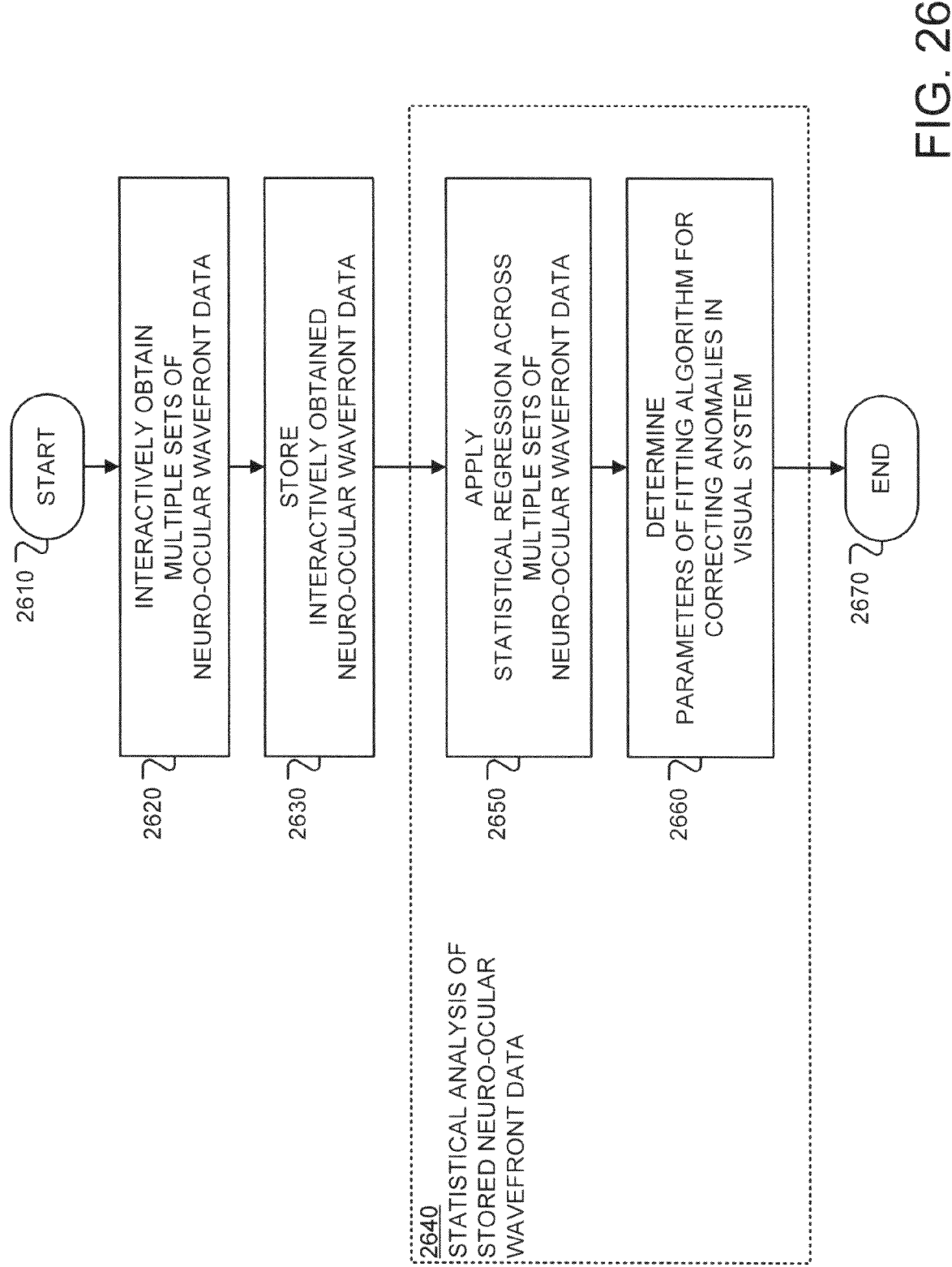

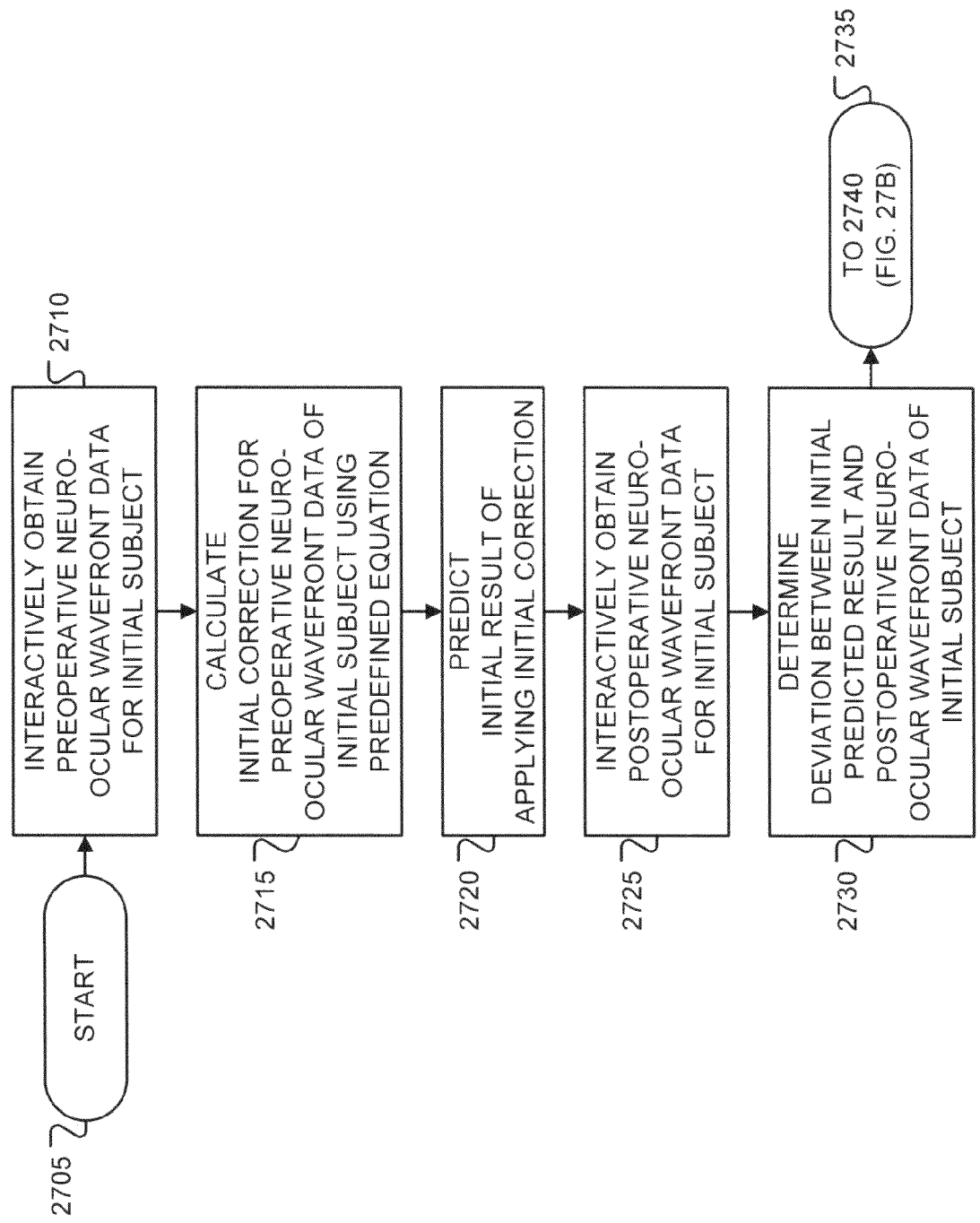

| Column | Variable Name | Definition |
|---|---|---|
| 1 | Point ID | A unique point identifier that describes the location of the point in the pupil sampling map. The point (0,0) is given a Point ID of 0. |
| 2 | X coordinate (mm) | Horizontal location in entrance pupil where the acquisition occurred. |
| 3 | Y coordinate (mm) | Vertical location in entrance pupil where the acquisition occurred. |
| 4 | dx (milliradians) | Horizontal compensation measurement to nullify wavefront error at (x, y). |
| 5 | dy (milliradians) | Vertical compensation measurement to nullify wavefront error at (x, y). |

FIG. 28

| Variables | Definition |
|---|---|
| (x, y) | Coordinate system of wavefront measurement with respect to pupillary centroid. (0, 0) corresponds to centroid of pharmacologically dilated pupil in mesopic illumination conditions. |
| (X, Y) | Coordinate system of ablation profile with respect to corneal vertex. (0, 0) corresponds to corneal vertex. |

FIG. 29

| Variable Name | Definition |
|---|---|
| $R_{OZ}$ | Radius of optical zone. |
| $R_{TZ}$ | Radius of transition zone. |
| $W_{min}$ | Minimum value of the wavefront error over the optical zone area (the most negative value). |
| $D_{Mes}$ | Diameter of the natural pupil under mesopic illumination conditions. |
| $D_{Dil}$ | Diameter of the pharmacologically dilated pupil under mesopic illumination conditions. |
| $\eta$ | Ablation rate efficacy factor, $\eta = 1.0$ (for corneal tissue), $\eta \approx 0.3$ (for polymethylmethacrylate, PMMA). |
| $r$ | Radius from the pupillary centroid to the point $(X,Y)$, $r = \sqrt{x^2 + y^2}$. |
| $n_c$ | Index of refraction of cornea ($n_c = 1.3771$), according to reference 4. |

FIG. 30

| Emory Vision Term Index | Zemax Term Number | OSA Term Number (Thibos, et. al.) | Zernike Function Term = $F_n(\rho, \theta)$ |
|---|---|---|---|
| Unused | 1 | 0 | 1 |
| 1 | 2 | 2 | $4^{(1/2)} (\rho) * \cos(\theta)$ |
| 2 | 3 | 1 | $4^{(1/2)} (\rho) * \sin(\theta)$ |
| 3 | 6 | 5 | $6^{(1/2)} (\rho^2) * \cos(2\theta)$ |
| 4 | 4 | 4 | $3^{(1/2)} (2\rho^2 - 1)$ |
| 5 | 5 | 3 | $6^{(1/2)} (\rho^2) * \sin(2\theta)$ |
| 6 | 10 | 9 | $8^{(1/2)} (\rho^3) * \cos(3\theta)$ |
| 7 | 8 | 8 | $8^{(1/2)} (3\rho^3 - 2\rho) * \cos(\theta)$ |
| 8 | 7 | 7 | $8^{(1/2)} (3\rho^3 - 2\rho) * \sin(\theta)$ |
| 9 | 9 | 6 | $8^{(1/2)} (\rho^3) * \sin(3\theta)$ |
| 10 | 14 | 14 | $10^{(1/2)} (\rho^4) * \cos(4\theta)$ |
| 11 | 12 | 13 | $10^{(1/2)} (4\rho^4 - 3\rho^2) * \cos(2\theta)$ |
| 12 | 11 | 12 | $5^{(1/2)} (6\rho^4 - 6\rho^2 + 1)$ |
| 13 | 13 | 11 | $10^{(1/2)} (4\rho^4 - 3\rho^2) * \sin(2\theta)$ |
| 14 | 15 | 10 | $10^{(1/2)} (\rho^4) * \sin(4\theta)$ |
| 15 | 20 | 20 | $12^{(1/2)} (\rho^5) * \cos(5\theta)$ |
| 16 | 18 | 19 | $12^{(1/2)} (5\rho^5 - 4\rho^3) * \cos(3\theta)$ |
| 17 | 16 | 18 | $12^{(1/2)} (10\rho^5 - 12\rho^3 + 3\rho) * \cos(\theta)$ |
| 18 | 17 | 17 | $12^{(1/2)} (10\rho^5 - 12\rho^3 + 3\rho) * \sin(\theta)$ |
| 19 | 19 | 16 | $12^{(1/2)} (5\rho^5 - 4\rho^3) * \sin(3\theta)$ |
| 20 | 21 | 15 | $12^{(1/2)} (\rho^5) * \sin(5\theta)$ |
| 21 | 28 | 27 | $14^{(1/2)} (\rho^6) * \cos(6\theta)$ |
| 22 | 26 | 26 | $14^{(1/2)} (6\rho^6 - 5\rho^4) * \cos(4\theta)$ |
| 23 | 24 | 25 | $14^{(1/2)} (15\rho^6 - 20\rho^4 + 6\rho^2) * \cos(2\theta)$ |
| 24 | 22 | 24 | $7^{(1/2)} (20\rho^6 - 30\rho^4 + 12\rho^2 - 1)$ |
| 25 | 23 | 23 | $14^{(1/2)} (15\rho^6 - 20\rho^4 + 6\rho^2) * \sin(2\theta)$ |
| 26 | 25 | 22 | $14^{(1/2)} (6\rho^6 - 5\rho^4) * \sin(4\theta)$ |
| 27 | 27 | 21 | $14^{(1/2)} (\rho^6) * \sin(6\theta)$ |
| 28 | 36 | 35 | $16^{(1/2)} (\rho^7) * \cos(7\theta)$ |
| 29 | 34 | 34 | $16^{(1/2)} (7\rho^7 - 6\rho^5) * \cos(5\theta)$ |
| 30 | 32 | 33 | $16^{(1/2)} (21\rho^7 - 30\rho^5 + 10\rho^3) * \cos(3\theta)$ |
| 31 | 30 | 32 | $16^{(1/2)} (35\rho^7 - 60\rho^5 + 30\rho^3 - 4\rho) * \cos(\theta)$ |
| 32 | 29 | 31 | $16^{(1/2)} (35\rho^7 - 60\rho^5 + 30\rho^3 - 4\rho) * \sin(\theta)$ |
| 33 | 31 | 30 | $16^{(1/2)} (21\rho^7 - 30\rho^5 + 10\rho^3) * \sin(3\theta)$ |
| 34 | 33 | 29 | $16^{(1/2)} (7\rho^7 - 6\rho^5) * \sin(5\theta)$ |
| 35 | 35 | 28 | $16^{(1/2)} (\rho^7) * \sin(7\theta)$ |

FIG. 31

APPLICATION OF NEURO-OCULAR WAVEFRONT DATA IN VISION CORRECTION

CROSS REFERENCE TO RELATED APPLICATIONS

This application is a divisional application of U.S. patent application Ser. No. 10/811,368, filed on Mar. 26, 2004 now U.S. Pat. No. 7,703,919 which claims the benefit of U.S. provisional patent application Ser. No. 60/458,480, filed on Mar. 28, 2003, and having the title "Systems and Methods for Measuring, Correcting, and Optimizing Vision," which is incorporated herein by reference in its entirety.

STATEMENT RELATED TO COLOR DRAWINGS

The patent or application file contains at least one drawing executed in color. Copies of this patent or patent application publication with color drawings(s) will be provided by the Office upon request and payment of the necessary fee.

COPYRIGHT NOTICE

A portion of the disclosure of this patent document contains material, which is subject to copyright protection. The copyright owner has no objection to the facsimile reproduction by anyone of the patent document or patent disclosure as it appears in the U.S. Patent and Trademark Office patent file or records, but otherwise reserves all copyright rights whatsoever.

TECHNICAL FIELD

The present disclosure relates generally to metrics and, more particularly, to visual metrics associated with vision correction.

BACKGROUND

Traditionally, visual acuity has been measured using eye charts, in which subjects interactively provided vision-related information by reading characters of various sizes from the eye chart. The refractive error of the eye has traditionally been determined by having the subject recursively view objects through various sphero-cylindrical lenses, and selecting the combination of lenses that provides the clearest image. While such acuity and refraction measurements are still widely used, they provide only gross measurements of the visual system.

Unlike refraction, ocular aberrometry provides greater details with reference to the refractive properties of the eye. In ocular aberrometry, the refractive properties of the eye are measured using various lenses and projections, typically sampling multiple points across the pupil rather than a single measurement as performed during refraction, thereby providing more detailed information on higher-order optical anomalies. The aberration information provided by ocular aberrometers is designated herein as "ocular wavefront error." Examples of ocular aberrometers and ocular aberrometry are disclosed in U.S. Pat. Nos. 5,777,719, 6,095,651, and 6,511,180, which are incorporated herein by reference in their entireties.

While ocular aberrometers provide detailed information on the optical characteristics of the eye, these devices usually provide no information with reference to the neurological pathways between the eye and the brain and they are not capable of localizing the retinal plane preferred by the patient. In other words, the integrated visual pathway between the eye and the brain can introduce another transfer function, which is undetectable by ocular aberrometry.

In order to address these deficiencies, a technique known as visual aberrometry has been developed, in which the patient's preferred retinal plane is localized and the effects of the neurological pathways are taken into account by combining subject feedback with the physio-optical characteristics of the eye. The aggregate effect of the neurological pathway in combination with the characteristics of the eye is referred to herein as "neuro-ocular wavefront error" or "neuro-ocular wavefront data." Examples of visual aberrometers are described in greater detail in U.S. Pat. Nos. 6,000,800 and 6,099,125, which are incorporated herein by reference in their entireties.

Visual aberrometry, and the acquisition of neuro-ocular wavefront data, is still relatively new and continually improving. Along with the continued development of visual aberrometry, there is corresponding effort to exploit the full potential of visual aberrometry.

SUMMARY

The present disclosure provides systems and methods for diagnosing and treating subjects using neuro-ocular wavefront data. As such, in some embodiments, among others, neuro-ocular wavefront data is obtained, and one or more characteristics of a visual system are ascertained from the neuro-ocular wavefront data.

Other systems, devices, methods, features, and advantages will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 13 is a diagram showing an embodiment of a subject data entry screen for a refractometer adapted to acquire neuro-ocular wavefront data.

FIG. 21 is a flowchart showing, in greater detail, an embodiment of the step of correlating neuro-ocular wavefront data to vision parameters, from FIG. 17.

FIG. 26 is a flowchart showing an embodiment of a method for acquiring and processing neuro-ocular wavefront data, in which multiple sets of data are statistically analyzed.

FIGS. 27A and 27B are flowcharts showing another embodiment of a method for acquiring and processing neuro-ocular wavefront data, in which multiple sets of data are statistically analyzed.

FIG. 28 is a table showing definitions of various variables related to the locations of sampling points and their respective corrections.

FIG. 29 is a table showing definitions of the coordinate systems in FIG. 9.

FIG. 30 is a table showing variable definitions used for computation of an ablation profile from acquired neuro-ocular wavefront data, as described with reference to FIG. 10.

FIG. 31 is a table showing an example list of Zernike function terms.

DETAILED DESCRIPTION OF THE EMBODIMENTS

Figure 1:
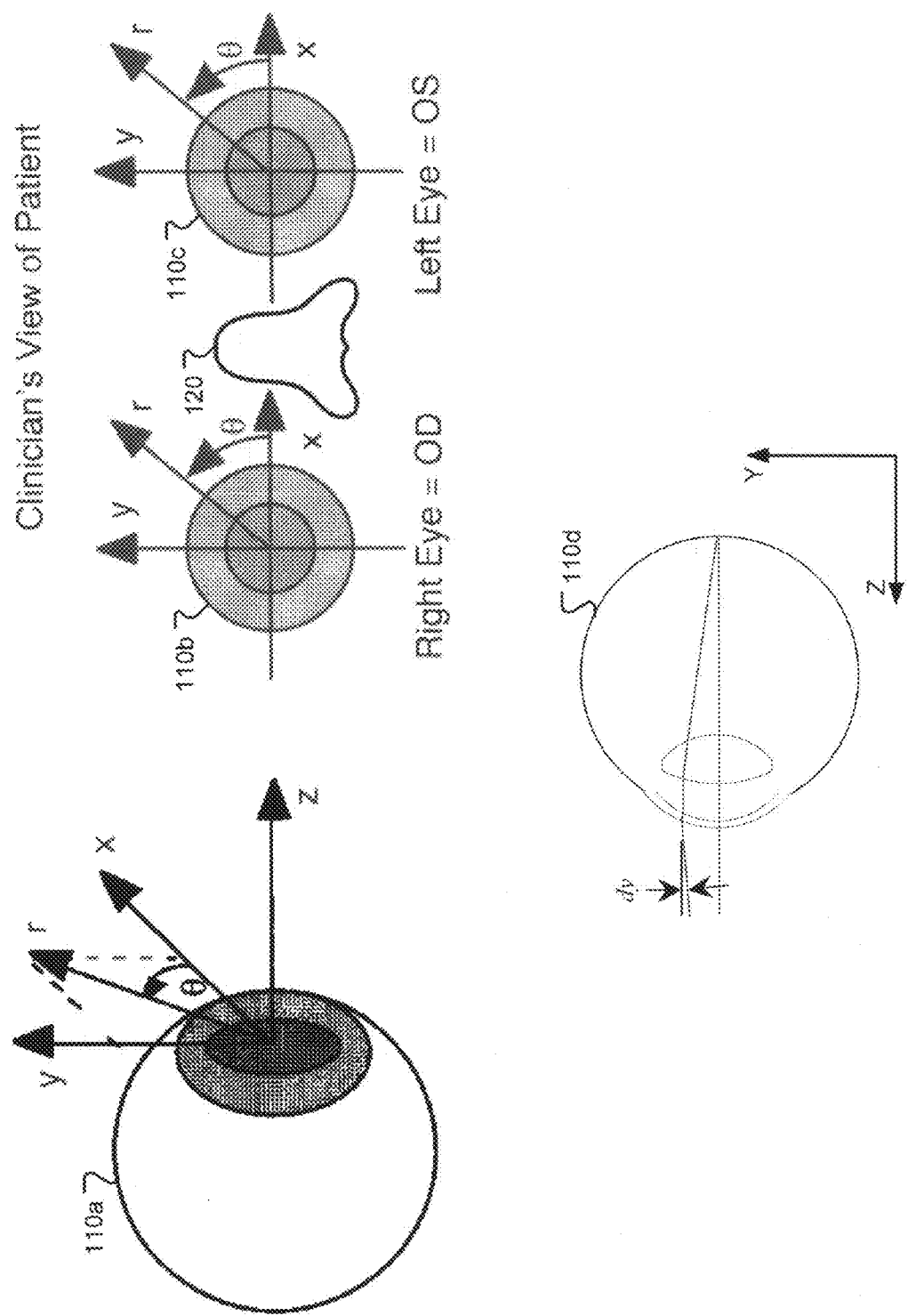
FIG. 1 is a diagram illustrating an eye, and various axes defined in relation to the eye.

Reference is now made in detail to the description of the embodiments as illustrated in the drawings. While several embodiments are described in connection with these drawings, there is no intent to limit the invention to the embodiment or embodiments disclosed herein. On the contrary, the intent is to cover all alternatives, modifications, and equivalents.

As noted above, traditional approaches to vision correction include measuring vision with visual acuity determined by eye charts and measuring the refractive error of the eye with test lenses. More advanced approaches employ ocular aberrometry, which provides greater details on the refractive properties of the eye. While both of these approaches provide useful results for vision correction, they are nonetheless deficient in many ways. For example, visual acuity provides nothing more than a gross estimate of the performance of the patient's visual system. Refraction provides only the best sphero-cylindrical correction that is averaged across the pupil. Ocular aberrometry, while providing more detailed refractive characteristics of the eye, provides no information on the preferred retinal plane and no information related to the neurological pathways associated with the eyes.

An improvement to both refraction and ocular aberrometry is visual aberrometry, in which the patient preferred retinal plane and the effects of the neurological pathways are taken into account by incorporating a subject feedback in a testing process that assesses multiple points within the pupil. The aggregate effect of the location of the patient's preferred retinal plane and the effects of the neurological pathways, is known as a "neuro-ocular wavefront error" or "neuro-ocular wavefront data." The present disclosure provides various systems and methods for exploiting the full potential of visual aberrometry. In other words, the present disclosure provides systems and methods in which neuro-ocular wavefront data can be used for diagnosis, treatment, or a combination of both.

In that regard, in some embodiments, neuro-ocular wavefront data is obtained from a subject (or, more specifically, a patient) and, thereafter, processed. In one embodiment, among others, processing of the neuro-ocular wavefront data includes correlating the neuro-ocular wavefront data with various subject-dependent or procedure-dependent parameters (hereinafter referred to in the aggregate as "vision parameters"). For example, the neuro-ocular wavefront data is often represented as an equation. Specifically, for vision correction, an example equation may be a Zernike polynomial with multiple coefficients. The coefficients in the Zernike polynomial, either alone or in combination with other coefficients, represents a particular characteristic of the patient's visual system.

In other embodiments, the correlated information is used for designing treatments. In some embodiments, the treatment can be designed by inverting the neuro-ocular wavefront data. For example, if the neuro-ocular wavefront error is defined by a Zernike polynomial, then the inversion of the polynomial provides one or more correction factors that can be applied, thereby effectively correcting for the apparent error that is introduced by the aberrations in the neuro-ocular system. For some embodiments, the inversion of the equation can be computationally derived using a least-squares fitting algorithm, a minimization algorithm, or other algorithms designed for curve fitting. Specifically, for neuro-ocular wavefront data that is represented by a Zernike polynomial, various coefficients of the Zernike polynomial may provide information on the near-vision or far-vision refraction sphere, refraction cylinder, and refraction axis. The curve-fitting algorithm provides information on how much correction will be needed to remedy the errors introduced by the refraction sphere, refraction cylinder, and/or refraction axis and the higher order aberrations of the visual system that are not corrected by sphero-cylindrical corrections.

Having described general concepts associated with various embodiments of the invention, attention is turned to FIGS. 1 through 27B, which provide greater details related to various embodiments of systems and methods for acquiring and processing neuro-ocular wavefront data.

FIG. 1 is a diagram illustrating an eye 110a, and various axes defined in relation to the eye 110a. Specifically, FIG. 1 shows the right eye 110b, the left eye 110c, and the nose 120 from the viewpoint of the clinician (or other individual performing the test on the subject). The coordinate system is right-handed insofar as the horizontal axis x extends from the left of the clinician (right of the subject) to the right of the clinician (left of the subject). The vertical axis y extends inferior to superior. Thus, the negative y-axis extends downward (toward the feet) while the positive y-axis extends upward (toward the head of the subject).

The x-axis and the y-axis define the pupillary plane. Since the corneal plane is parallel to the pupillary plane, the x-y plane also defines the corneal plane. The z-axis is defined as the axis normal to the pupillary plane. In that regard, the direction of light propagation in the eye 110a is defined by the positive z-axis. Due to the spherical nature of the eyes 110b, 110c (hereinafter simply referred to as 110), the coordinate system is defined using polar coordinates, where r represents the radius from the x-y origin, and θ represents the angle measured between the ray projected from (0, 0) to (x, y) with positive angles corresponding to counter-clockwise rotations. The normalized radius, is computed by taking the radius, r, and dividing by a normalization radius, $r_{norm}$. In this document, in most cases, $r_{norm}$ is taken to be 3.5 mm.

Additionally, FIG. 1 shows a compensation angle dy along the y-axis. This angle is the angular deviation that corresponds to a degree of refractive error, along the y-direction, for a given point on the eye. It should be appreciated that there is a similar compensation angle dx along the x-direction. The two compensation angles dx, dy provide an indication of a correction, as described in greater detail below. For simplicity, a summary of these variables is provided in FIG. 28.

Figure 2:
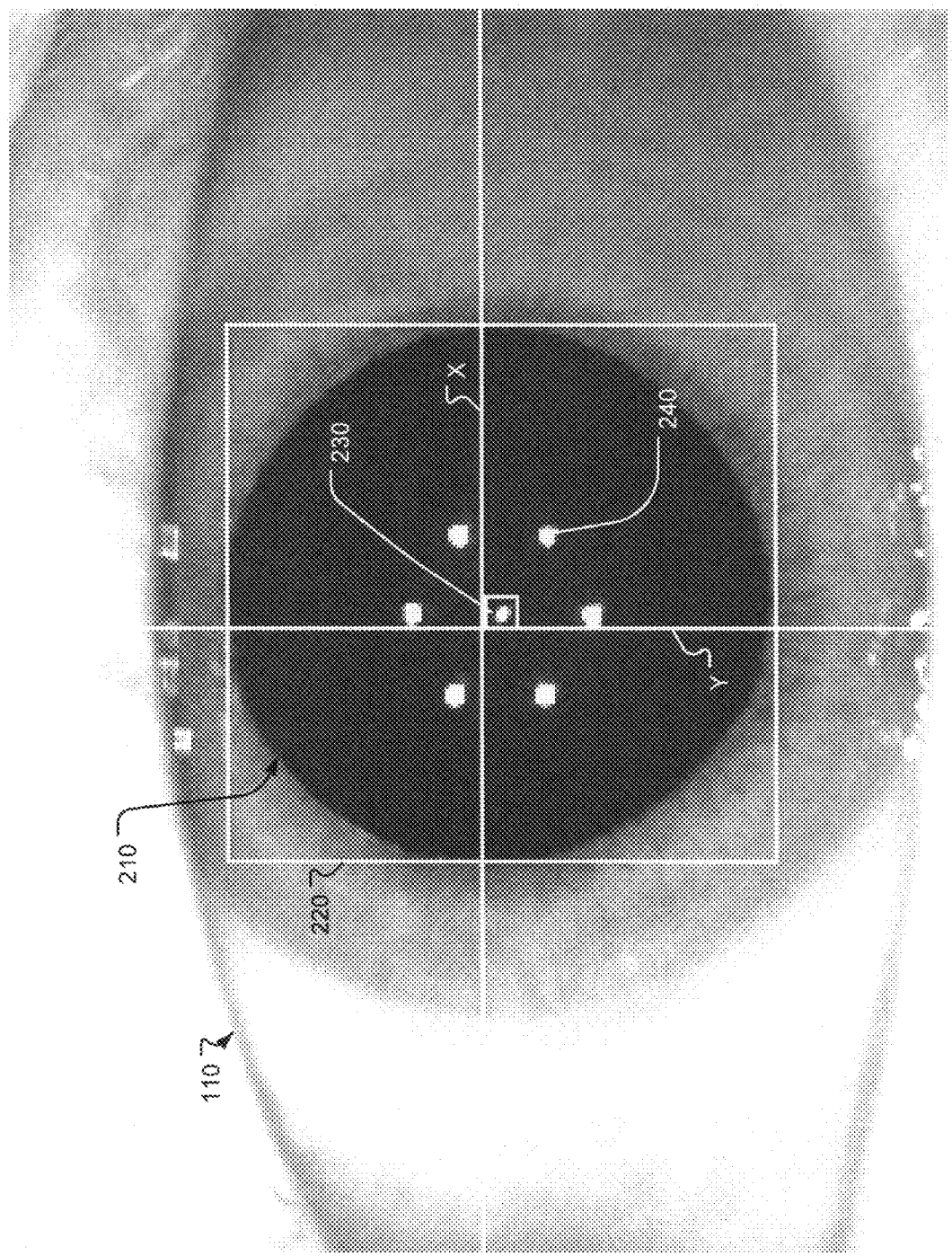
FIG. 2 is a diagram illustrating an embodiment of a pupillometry image, which may be used in a refractometer adapted to acquire neuro-ocular wavefront data.

FIG. 2 is a diagram illustrating an embodiment of a pupillometry image, which may be used in a refractometer adapted to acquire neuro-ocular wavefront data. An example of an aberrometer adapted to acquire neuro-ocular wavefront data can be found in U.S. Pat. No. 6,000,800 (hereinafter, "the '800 patent"), which is incorporated herein by reference, as if set forth in its entirety. For simplicity, the visual refractometer of the '800 patent is also referred to as the "InterWave" refractometer.

As shown in FIG. 2, the pupillometry image includes an image of the eye 110, which includes a pupil 210. For proper orientation, both the x-axis and the y-axis are shown in FIG. 2. In addition to the image of the eye 110 and the pupil 210, the pupillometry image includes a pupil tracking box 220, which dynamically tracks the movement of the pupil 210. Thus, the motion of the pupil tracking box 220 is substantially synchronous with the motion of the pupil 210.

In some embodiments, the pupil 210 is tracked using a first Purkinje image tracking method, which uses a camera and light source to compute the eye's orientation based on light reflections from the anterior surface of the cornea. Because the Purkinje tracking method does not depend on the pupil opening and closing concentrically about the eye's optic axis, the Purkinje tracking method is relatively accurate. However, the Purkinje tracking method often requires a stringently-controlled lighting environment to be able to detect the rear surface reflection off the eye's lens. For those embodiments that utilize the Purkinje tracking method, the pupillometry image also includes a location of the first Purkinje image (hereinafter, "the Purkinje location") 230, in addition to images from multiple eye-illumination light emitting diodes (LEDs) 240. While the Purkinje tracking method is specifically disclosed, it should be appreciated that other eye-tracking methods can be employed, as should be appreciated by those having skill in the art.

Figure 3:
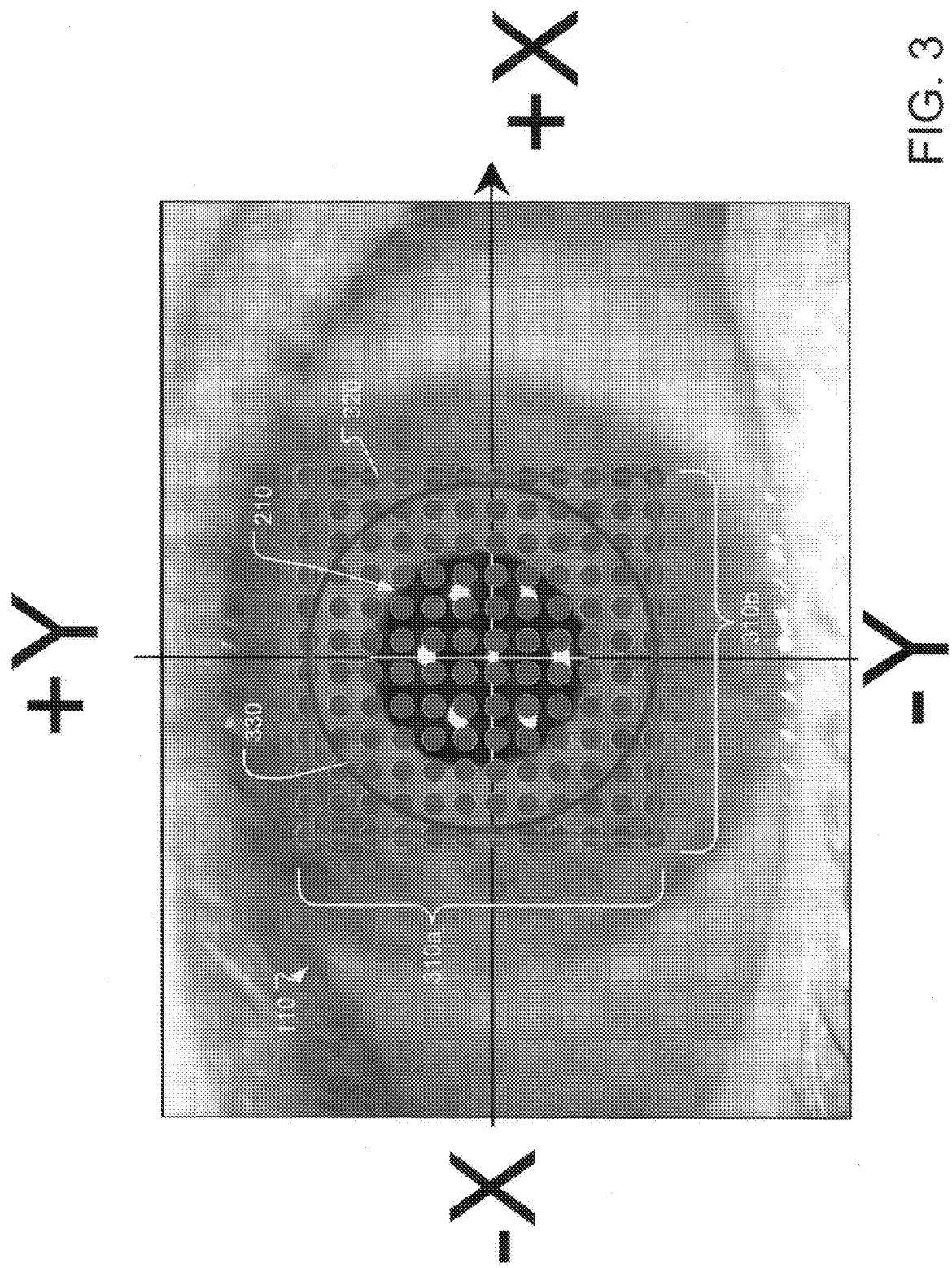
FIG. 3 is a diagram illustrating an embodiment of a sampling matrix in a refractometer adapted to acquire neuro-ocular wavefront data.
Figure 4:
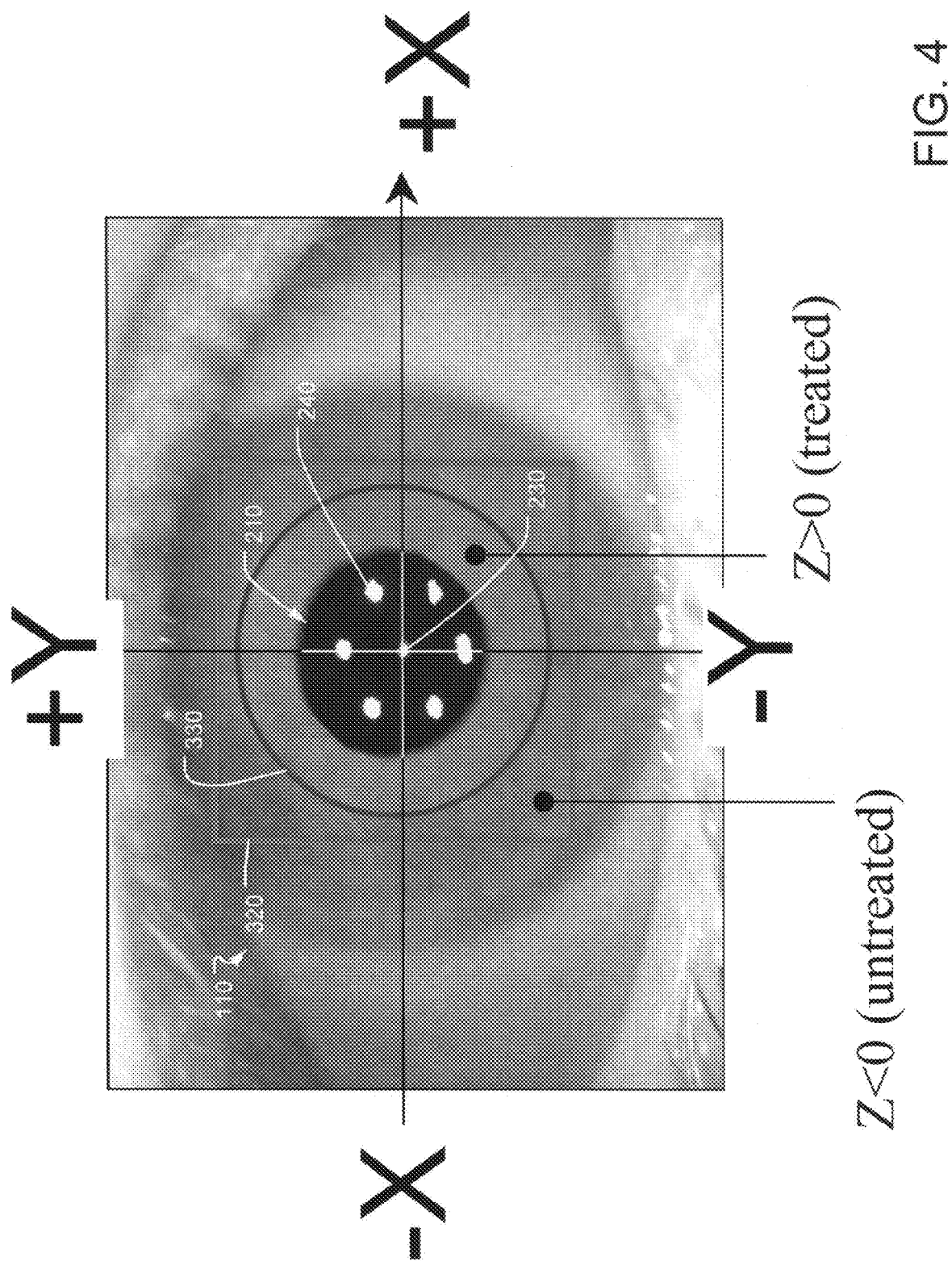
FIG. 4 is a diagram showing, more clearly, the treatment envelope of FIG. 3.

FIG. 3 is a diagram illustrating an embodiment of a sampling matrix 320 in a refractometer adapted to acquire neuro-ocular wavefront data. Again, for proper orientation, both the x-axis and the y-axis are shown in FIG. 3. The sampling matrix 320 superimposes onto the location of the pupil 210 as identified by the various LED images 230, 240. As shown in FIG. 3, in some embodiments, the sampling matrix 320 comprises multiple sampling elements 310a, 310b (hereinafter "sampling elements 310") that are arranged to form a grid-like pattern. A treatment envelope 330 within the sampling matrix 320 defines the area for treatment. This is shown more clearly in FIG. 4, where the treatment envelope 330 and the sampling matrix 320 are shown without the sampling elements 310.

Figure 5:
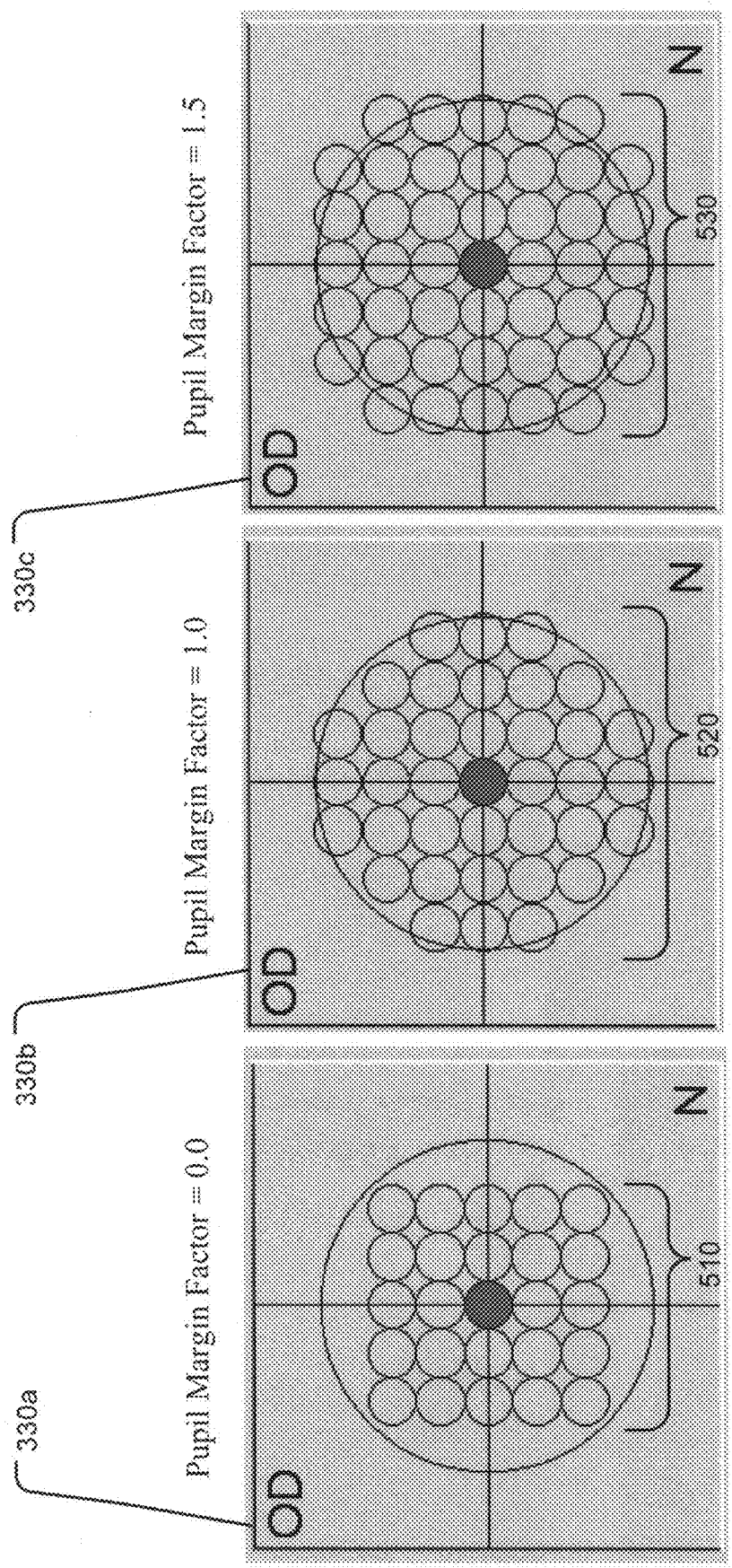
FIG. 5 is a diagram showing embodiments of various pupil-sampling maps.

FIG. 5 is a diagram showing embodiments of various treatment envelopes 330a . . . 330c (hereinafter referred to as "pupil-sampling maps 330"). The left-most image of FIG. 5 shows a reduced sampling map 510 that includes a square matrix that is wholly located within the treatment envelope. The center image of FIG. 5 shows a nominal sampling map 520, which includes sampling points that are substantially within the treatment envelope. The right-most image of FIG. 5 shows an increased sampling map 530, which includes any sampling point that intersects the treatment envelope. In that regard, it should be appreciated that a sampling matrix associated with the pupillometric measurements can be defined in various ways.

Figure 6:
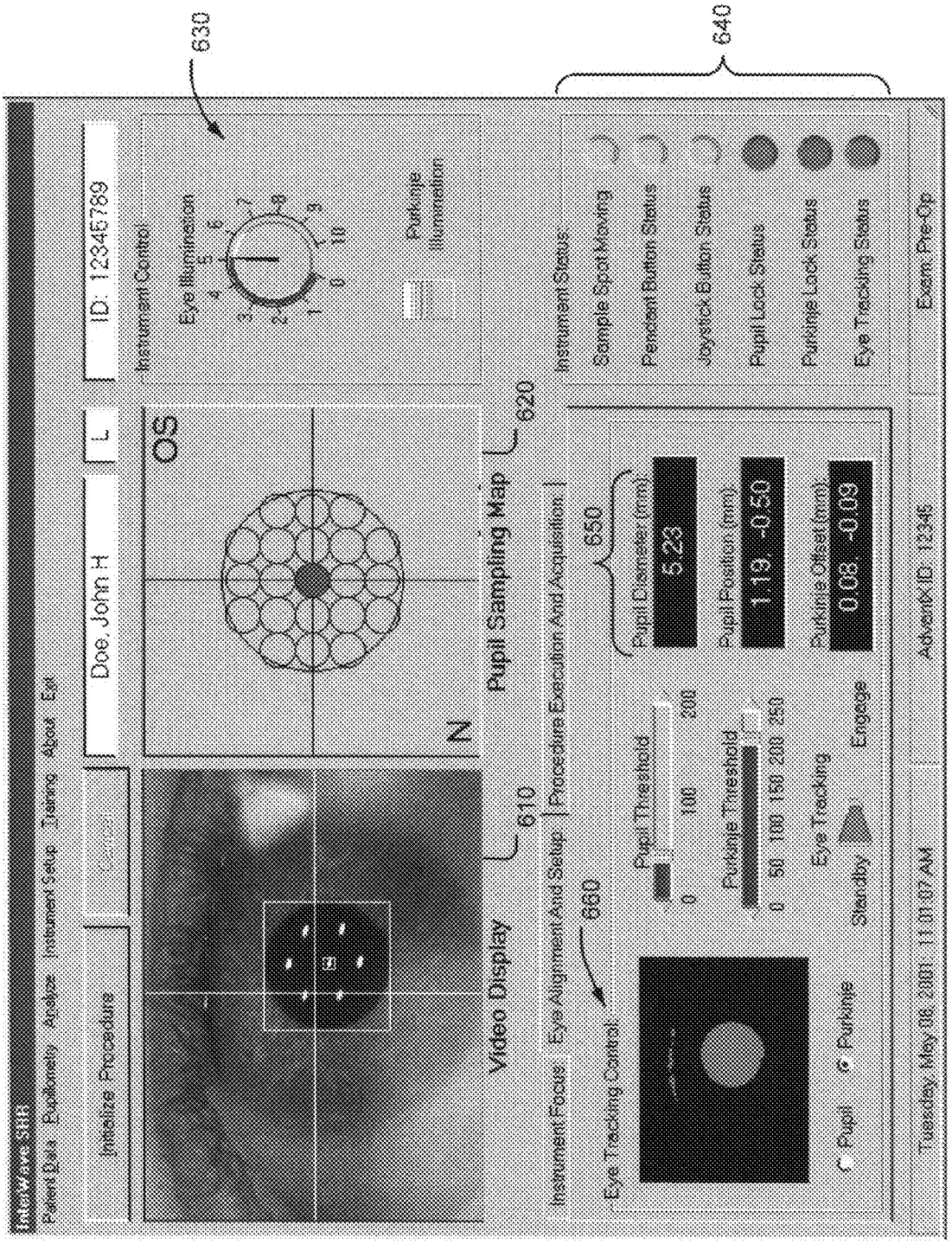
FIG. 6 is a diagram showing an example of an operator's display console of a refractometer adapted to acquire neuro-ocular wavefront data.
Figure 7:
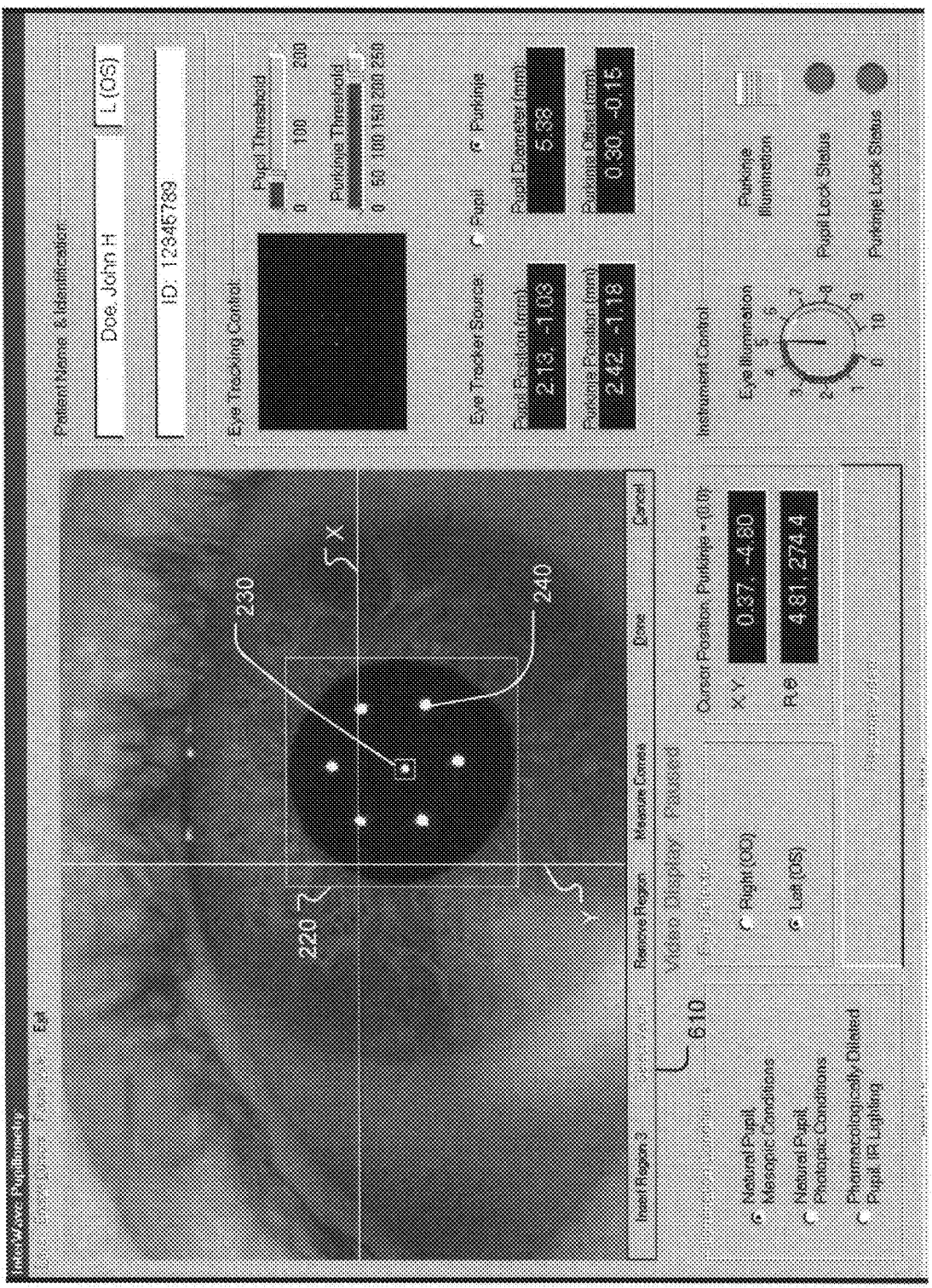
FIG. 7 is a diagram showing another example of the operator's display console of a refractometer adapted to acquire neuro-ocular wavefront data.

FIG. 6 is a diagram showing an example video display of a refractometer adapted to acquire neuro-ocular wavefront data. As shown in FIG. 6, the video display includes an eye display 610, which shows the pupil tracking box and the Purkinje location with reference to the x-y plane. Additionally, the video display comprises a sampling map 620, which shows the sampling points for acquiring the neuro-ocular wavefront data. Additionally, the video display includes an instrument control panel 630, which permits an operator to adjust various parameters associated with pupillometry. For example, for embodiments that employ the Purkinje tracking method, the instrument control panel 630 can include a graphical interface for adjusting the Purkinje illumination. In some embodiments, the video display can further include an instrument status panel 640, which apprises the operator of whether or not the instrument is properly operating. Additionally, the video display can include a tracking control display 660, which can include various settings and measurements 650, such as, for example, the measured pupil diameter, the pupil position, and the Purkinje offset. While specific display parameters are shown in FIG. 6, it should be appreciated that the video display can be configured to include other parameters of interest to the operator. Examples of other display parameters are shown in FIG. 7.

Figure 8:
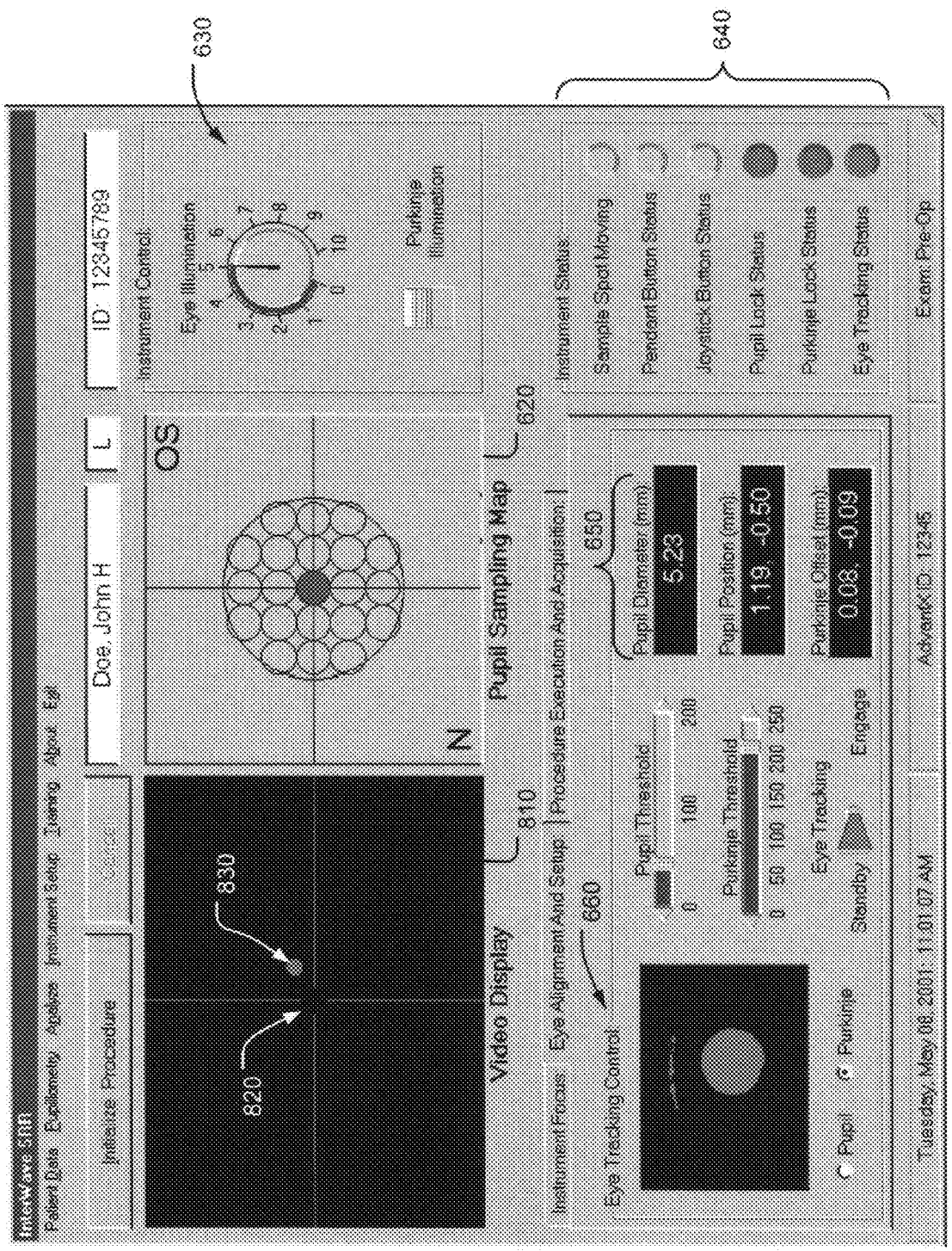
FIG. 8 is a diagram showing a display console with a sample alignment target and a test spot.

FIG. 8 is a diagram showing a video display with an alignment target and a test spot. The diagram of FIG. 8 is substantially identical to the diagram of FIG. 6, with the exception of the tracking display 810. Hence, only the tracking display 810 is discussed in detail with reference to FIG. 8. As shown in FIG. 8, the tracking display 810 comprises an alignment target 820 and a test spot 830. In the embodiment shown, the alignment target 820 is configured as cross-hairs while the test spot 830 is configured as a spot. Specifically, the tracking display 810 represents an image that is displayed to the subject. In that regard, for each of the sampling points in the sampling map 620, the subject is requested to interactively move the test spot 830 to the center of the alignment target 820. This process is repeated for each of the sampling points in the sampling map 620. Thus, for example, given the 21-point sampling matrix of FIG. 8, the refractometer interactively receives the first alignment data from the subject. Upon receiving the first alignment data, the next sampling point is selected, and the subject repeats the process for the second alignment data. The acquisition of all alignment data, in effect, represents the interactive acquisition of the neuro-ocular wavefront data. From the obtained data, a correction is then calculated. In some embodiments, the calculation of the correction can be seen as the estimation of one or more correction factors. Once data has been collected from all of the sampling points, the collected data can be used to reconstruct the neuro-ocular wavefront as follows.

The neuro-ocular wavefront can be represented as a Zernike polynomial according to:

$$W(x, y) = r_{norm} \sum_{n=1}^{Nt} C_n \cdot F_n(\rho, \theta) \quad [\text{Eq. 1}]$$

where $r_{norm}$ is the normative radius, $F_n(\rho,\theta)$ are the Zernike function terms, and $C_n$ are the coefficients for the neuro-ocular wavefront and $N_t$ is the number of coefficients used to define W. Eq. 1 can be re-written as:

$$W(x, y) = \sum_{n=1}^{Nt} B_n \cdot F_n(\rho, \theta) \quad [\text{Eq. 2}]$$

where:

$$B_n = r_{norm} \cdot C_n \quad [\text{Eq. 3}]$$

Given the coordinate system, as defined in FIG. 1, a given sampling point (x,y) on the sampling map can be defined according to:

$$x = \rho \cos(\theta), \, y = \rho \sin(\theta) \quad [\text{Eq. 4}]$$

with:

$$\rho = \frac{\sqrt{x^2 + y^2}}{r_{norm}}, \quad 0 \leq \sqrt{x^2 + y^2} \leq r_{max} \quad [\text{Eq. 5}]$$

where $r_{max}$ is the largest radius within the sampling map.

As noted with reference to FIG. 1, the degree of aberration at any sampling point can be defined by the compensation angles:

$$dx(x, y) = +\frac{\partial W}{\partial x} \quad [\text{Eq. 6}]$$

and:

$$dy(x, y) = +\frac{\partial W}{\partial y}. \quad [\text{Eq. 7}]$$

Since the neuro-ocular wavefront data can be represented in accordance with Eq. 1, the solution of Eq. 1 can be used to determine various neuro-ocular characteristics as well as various treatments for neuro-ocular aberrations. In other words, the neuro-ocular system can be characterized by solving for the various coefficients in Eq. 1, and these solutions can be used to design various treatments.

The specific neuro-ocular wavefront of Eq. 1 can be written generically as:

$$f(x) = \sum_{k=1}^{N} a_k X_k(x) \quad [\text{Eq. 8}]$$

where $X_k(x)$ is the basis function for $f$, and $a_k$ is the coefficient associated with its respective basis function. Given Eq. 8, the solutions for coefficients can be obtained using a least-squares algorithm (or any other fitting routine) such that the merit function:

$$\chi^2 = \sum_{i=1}^{M} \left[ f_i - \sum_{k=1}^{N} a_k X_k(x_i) \right]^2 \quad [\text{Eq. 9}]$$

is minimized. Defining $$\alpha = dx \quad [\text{Eq. 10}]$$

and $$\beta = dy \quad [\text{Eq. 11}],$$

the compensation angles for each sampling point can be represented as:

$$\alpha(x, y) = r_{norm} \sum_{n=1}^{Nt} C_n \frac{\partial F_n}{\partial x} = \sum_{n=1}^{Nt} C_n G_n \quad [\text{Eq. 12}]$$

and:

$$\beta(x, y) = r_{norm} \sum_{n=1}^{Nt} C_n \frac{\partial F_n}{\partial y} = \sum_{n=1}^{Nt} C_n H_n. \quad [\text{Eq. 13}]$$

where:

$$G_n = r_{norm} \cdot \frac{\partial F_n}{\partial x} \quad [\text{Eq. 14}]$$

and:

$$H_n = r_{norm} \cdot \frac{\partial F_n}{\partial y} \quad [\text{Eq. 15}]$$

While Eq. 9 provides the merit function for a single-variable equation, it is clear from Eqs. 12 and 13 that the neuro-ocular wavefront is a function of two variables, namely, the compensation angle associated with the x-axis and the compensation angle associated with the y-axis. Thus, modifying Eq. 9 to accommodate two variables results in:

$$\chi^2 = \sum_{i=1}^{Np}\left\{\left[\alpha_i - \sum_{n=1}^{Nt}C_nG_{n(x_i,y_i)}\right]^2 + \left[\beta_i - \sum_{n=1}^{Nt}C_nH_{n(x_i,y_i)}\right]^2\right\}. \quad [\text{Eq. 16}]$$

Solutions to $C_n$ are determined by:

$$\sum_{i=1}^{Np}\left[\alpha_i - \sum_{j=1}^{Nt}C_jG_{j(x_i,y_i)}\right]G_{n(x_i,y_i)} + \sum_{i=1}^{Np}\left[\beta_i - \sum_{j=1}^{Nt}C_jH_{j(x_i,y_i)}\right]H_{n(x_i,y_i)} = 0 \quad [\text{Eq. 17}]$$

where $N_p$ is the number of sample points and $$n\in(1,2,\ldots,N_t) \quad [\text{Eq. 18}].$$

Eq. 17 can be re-written as:

$$\sum_{i=1}^{Np}\sum_{j=1}^{Nt}C_jG_{j(x_i,y_i)}G_{n(x_i,y_i)} + \sum_{i=1}^{Np}\sum_{j=1}^{Nt}C_jH_{j(x_i,y_i)}H_{n(x_i,y_i)} = \sum_{i=1}^{Np}\alpha_iG_{n(x_i,y_i)} + \sum_{i=1}^{Np}\beta_iH_{n(x_i,y_i)} \quad [\text{Eq. 19}]$$

or $$\sum_{j=1}^{Nt}\left[\left(\sum_{i=1}^{Np}G_{j(x_i,y_i)}G_{n(x_i,y_i)}\right)C_j\right] + \sum_{j=1}^{Nt}\left[\left(\sum_{i=1}^{Np}H_{j(x_i,y_i)}H_{n(x_i,y_i)}\right)C_j\right] = \sum_{i=1}^{Np}\alpha_iG_{n(x_i,y_i)} + \sum_{i=1}^{Np}\beta_iH_{n(x_i,y_i)} \quad [\text{Eq. 20}]$$

Simplifying Eq. 20 into a single matrix operation results in:

$$\sum_{j=1}^{Nt}S_{nj}C_j = T_n \quad [\text{Eq. 21}]$$

where:

$$S_{nj} = \sum_{i=1}^{Np}G_{j(x_i,y_i)}G_{n(x_i,y_i)} + \sum_{i=1}^{Np}H_{j(x_i,y_i)}H_{n(x_i,y_i)} \quad [\text{Eq. 22}]$$

and:

$$T_n = \sum_{i=1}^{Np}\alpha_iG_{n(x_i,y_i)} + \sum_{i=1}^{Np}\beta_iH_{n(x_i,y_i)} \quad [\text{Eq. 23}]$$

Using matrix notation, Eq. 22 becomes:

$$S = G^TG + H^TH \quad [\text{Eq. 24}]$$

and Eq. 23 becomes:

$$T = G^T\alpha + H^T\beta \quad [\text{Eq. 25}]$$

Thus, $C_n$ is derived as a solution to:

$$T = SC \quad [\text{Eq. 26}]$$

where C is a vector that contains the Zernike function terms. Alternatively, Eq. 26 can be depicted as:

$$\begin{pmatrix}T_1\\T_2\\\ldots\\T_{Nt}\end{pmatrix} = \begin{pmatrix}S_{1,1} & S_{1,2} & \ldots & S_{1,Nt}\\S_{2,1} & S_{2,2} & \ldots & S_{2,Nt}\\& \ldots & &\\S_{Nt,1} & S_{Nt,2} & \ldots & S_{Nt,Nt}\end{pmatrix}\begin{pmatrix}C_1\\C_2\\\ldots\\C_{Nt}\end{pmatrix} \quad [\text{Eq. 27}]$$

to which the solution is:

$$C = inv(S)T \quad [\text{Eq. 28}]$$

or, written differently:

$$C_n = \sum_{j=1}^{Nt}\Omega_{nj}T_j \quad [\text{Eq. 29}]$$

where:

$$\Omega = inv(S) \quad [\text{Eq. 30}].$$

Typically, zero-reference measurements are made in order to remove any misalignment between the subject and the measurement instrument. The zero-reference is measured by calculating a baseline angular deviation associated with a central point at the entrance pupil of the subject. The reference measurements can be acquired multiple times and averaged in order to increase the accuracy of the zero-reference. The zero-references for the x-axis is given as:

$$dx_{i,saved} = dx_{i,acquired} - dx_{ref} \quad [\text{Eq. 31}]$$

while the zero-reference for the y-axis is given as:

$$dy_{i,saved} = dy_{i,acquired} - dy_{ref} \quad [\text{Eq. 32}]$$

For some instruments, such as the InterWave™ scanner, the neuro-ocular wavefront data is acquired with respect to the instrument's sphere-equivalent setting. Thus, for those instruments, it is desirable to correct the Zernike coefficients to account for the instrument setting. Given the Zernike function terms, as shown in FIG. 31, Eq. 1 can be expanded up to five terms as:

$$W(r,\theta) = C_1 \cdot r_{norm} \cdot 2\rho\cos\theta + C_2 \cdot r_{norm} \cdot 2\rho\sin\theta + C_3 \cdot r_{norm} \cdot \sqrt{6} \cdot \rho^2 \cdot \cos(2\theta) + C_4 \cdot r_{norm} \cdot \sqrt{3} \cdot (2\rho^2 - 1) + C_5 \cdot r_{norm} \cdot \sqrt{6} \cdot \rho^2 \cdot \sin(2\theta) + \text{higher order terms.} \quad [\text{Eq. 33}]$$

Since the Zernike function terms associated with the sphere and cylinder are $C_3$, $C_4$, and $C_5$, each of these terms can be corrected to account for the instrument's sphere-equivalent setting, such that:

$$C_3' = C_3 + \frac{D_{cyl} \cdot r_{norm} \cdot \cos(2 \cdot \theta_{axi})}{4 \cdot \sqrt{6}} \qquad [\text{Eq. 34}]$$

$$C_4' = C_4 - \frac{D_{sph} \cdot r_{norm}}{4 \cdot \sqrt{3}} - \frac{D_{cyl} \cdot r_{norm}}{8 \cdot \sqrt{3}} \qquad [\text{Eq. 35}]$$

and:

$$C_5' = C_5 + \frac{D_{cyl} \cdot r_{norm} \cdot \cos(2 \cdot \theta_{axi})}{4 \cdot \sqrt{6}} \qquad [\text{Eq. 36}]$$

where $D_{sph}$, $D_{cyl}$, and $\theta_{axi}$ represent the ophthalmic sphere value, the ophthalmic cylinder value, and the ophthalmic axis value, respectively, with:

$$D_{sph,CP} = \frac{D_{sph,MR}}{1 - T \cdot D_{sph,MR}} \qquad [\text{Eq. 37}]$$

and:

$$D_{cyl,CP} = \frac{D_{cyl,MR}}{1 - T \cdot D_{cyl,MR}} \qquad [\text{Eq. 38}]$$

where the subscript CP denotes the corneal plane and the subscript MR denotes the eyeglass plane.

Figure 9:
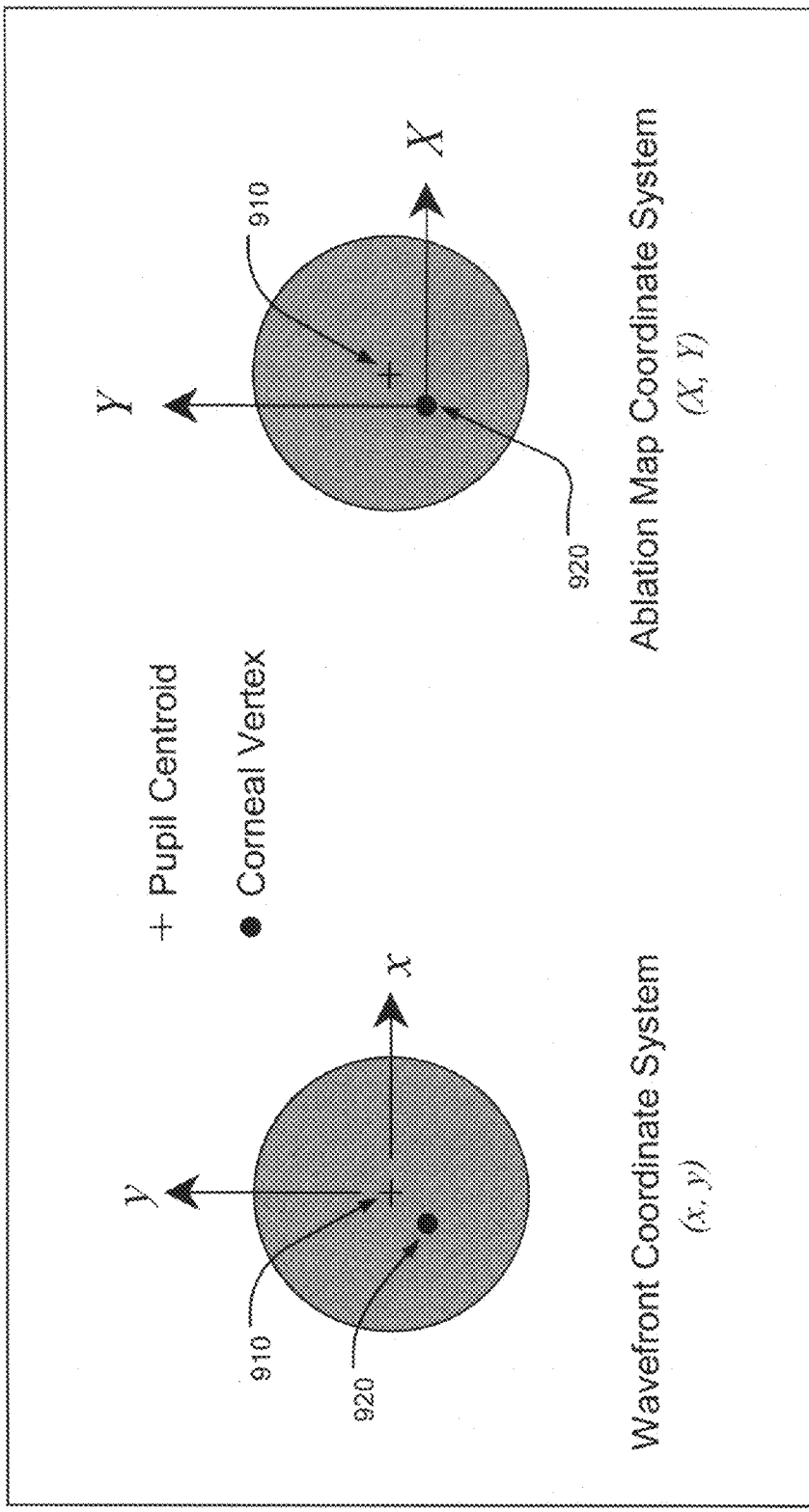
FIG. 9 is a diagram showing a coordinate system of the neuro-ocular wavefront data and a coordinate system for an ablation map that corresponds to the neuro-ocular wavefront data.
Figure 10:
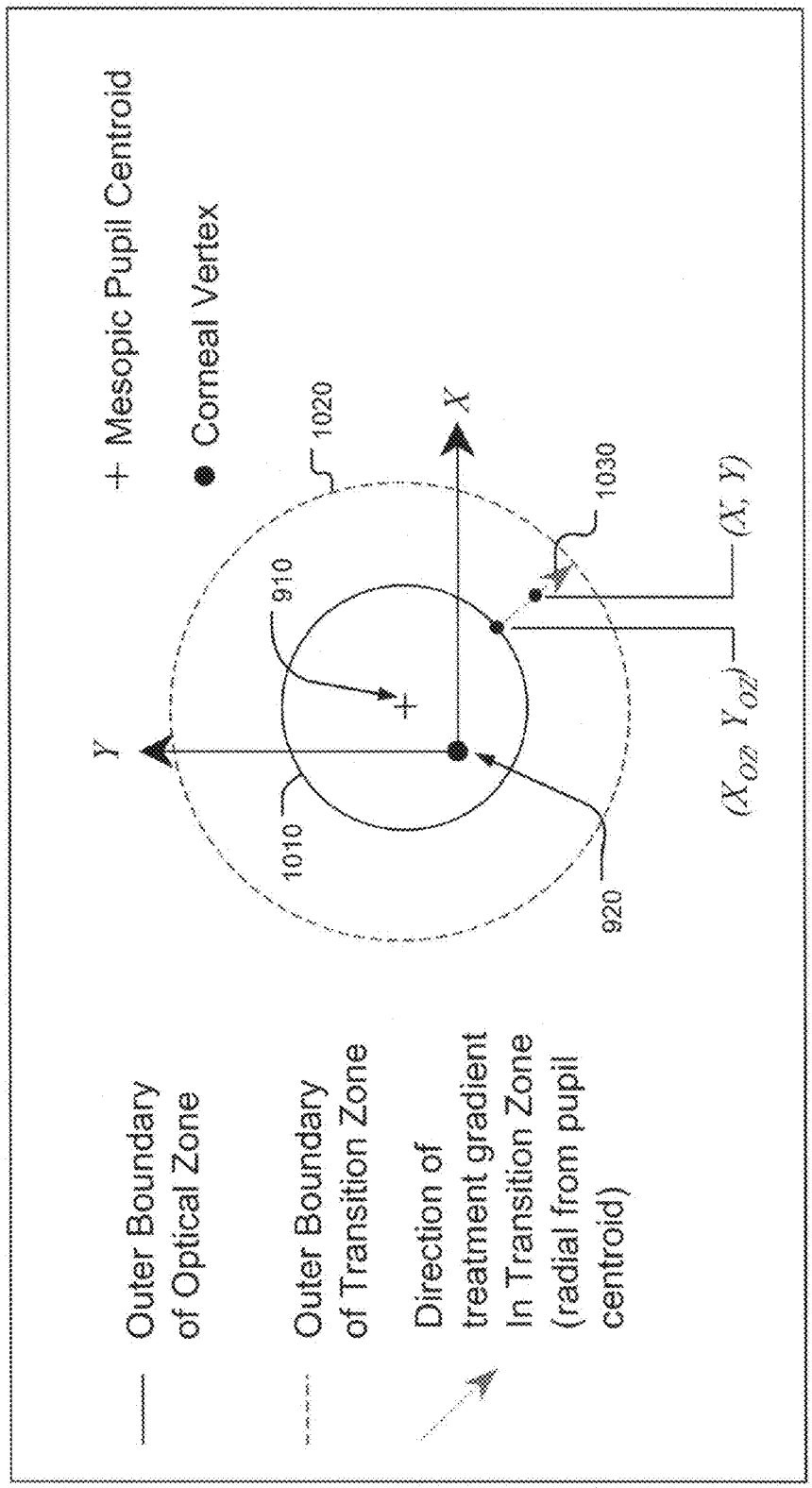
FIG. 10 is a diagram showing an optical zone and a transition zone associated with the ablation map of FIG. 9.

Given these solutions to Eq. 1, and their various modifications, an example of a correction obtained using these equations is shown with reference to FIGS. 9 and 10.

FIG. 9 is a diagram showing a coordinate system of the neuro-ocular wavefront data and a coordinate system for a laser ablation map, to be used to direct laser treatment in vision correction that corresponds to the neuro-ocular wavefront data. Specifically, FIG. 9 shows a wavefront coordinate system (left) and a coordinate system for laser ablation map (right). The wavefront coordinate system and the ablation map coordinate system have a congruent relationship to each other. For example, the center of the wavefront coordinate system is the pupil centroid 910. On the other hand, the center of the ablation map coordinate system is the corneal vertex 920. Thus, if the position of the corneal vertex 920 is known with reference to the location of the pupil centroid 910, then an appropriate adjustment can be calculated for the ablation map.

For example, presuming that the Purkinje location is coincident with the corneal vertex, if the Purkinje offset values are defined according to:

$$x_0 = \text{PurkinjeOffsetMMx} \qquad [\text{Eq. 39}]$$

and:

$$y_0 = \text{PurkinjeOffsetMMy} \qquad [\text{Eq. 40}],$$

then the coordinate systems of FIG. 9 are related to each other according to:

$$x = X + x_0 \qquad [\text{Eq. 41}]$$

and:

$$y = Y + y_0 \qquad [\text{Eq. 42}].$$

Given the relationship between the two coordinate systems, appropriate corrections can be calculated. Example procedures for calculating corrections are provided below, with reference to the flowcharts of FIGS. 17 through 27B. For simplicity, FIG. 29 provides a summary of the variables associated with the calculations in Eqs. 39 through 42.

FIG. 10 is a diagram showing an optical zone 1010 and a transition zone 1020 associated with the ablation map of FIG. 9. As shown in FIG. 10, a treatment profile can be represented as an aggregate of an optical zone treatment and a transition zone treatment according to:

$$T_{A-T}(X,Y) = T_{A-OZ}(X,Y) + T_{A-TZ}(X,Y) \qquad [\text{Eq. 43}].$$

where $T_{A-OZ}(X,Y)$ represents the treatment profile of the optical zone, and $A_{A-TZ}(X,Y)$ represents the treatment profile of the transition zone. Since the first two coefficients, $C_1$ and $C_2$, of Eq. 1 represent tilt of the wavefront error, which affects the fixation direction of each eye, these terms are effectively removed from ablation calculations by setting:

$$C_1 = 0 \qquad [\text{Eq. 44}]$$

and;

$$C_2 = 0 \qquad [\text{Eq. 45}].$$

For some embodiments, it may be desirable to modify the Zernike function terms associated with sphere and cylinder in order to apply a different sphero-cylinder correction than that predicted by the Zernike function terms themselves. For example, a particular subject may indicate a preference for different visual corrections than what would be predicted solely from the Zernike function terms. For those cases, the subject's input can be accommodated by modifying the $C_3$, $C_4$, and $C_5$ terms, as defined in Eqs. 34 through 36 and, also, as shown in FIG. 30. Since those modifications are described above, further discussion of such modifications is omitted here.

Given the definitions of FIG. 30, the treatment profile for the optical zone can be represented according to:

$$T_{A-OZ}(X, Y) = \frac{W(X + x_0, Y + y_0) - W_{min}}{(n_c - 1)}, (r \leq R_{OZ}) \qquad [\text{Eq. 46}]$$

$$T_{A-OZ}(X, Y) = 0, (r > R_{OZ})$$

where $R_{OZ}$ represents the radius of the optical zone, $W_{min}$ represents the minimum value of the wavefront error (or the most negative value of the wavefront error) over the area of the optical zone, and $n_c$ represents the index of refraction of the cornea. Additionally, from the definitions of FIG. 30, the treatment profile for the transition zone can be represented according to:

$$T_{A-TZ}(X, Y) = T_0, (r \leq R_{OZ}) \qquad [\text{Eq. 47}]$$

$$T_{A-TZ}(X, Y) = (T_0 + T_{A-Oz}(X_{OZ}, Y_{OZ})) \cdot$$

-continued $$\left(1 - \frac{(r - R_{OZ})}{(R_{TZ} - R_{OZ})}\right) \cdot f(x, y),$$

$$(R_{OZ} < r \leq R_{TZ})$$

$$T_{A-TZ}(X, Y) = 0, (r > R_{TZ})$$

where $T_0$ represents a constant ablation depth, which is added to facilitate the addition of the transition zone, $T_{A-OZ}(X_{OZ}, Y_{OZ})$ is the optical zone treatment amount at a point where the optical zone boundary intersects the vector from the pupil center to the point (X,Y), and r is the distance from the mesopic pupil center to the point (X,Y). In Eq. 47, the function $f(x,y)$ is a smoothing function that is configured to contour the boundary between the optical zone and the transition zone such that there is a smooth transition between these two zones. As such, in some embodiments, the smoothing function may be a supergaussian having the form:

$$f(x, y) = e^{-2\left(\frac{r}{r_0}\right)^{2 \cdot n}} \quad \text{[Eq. 48]}$$

where n is a non-zero, positive integer value.

In some embodiments, Eq. 43 can be modified to include any number of variables, such as, for example, optical parameters, subject parameters, and/or environmental parameters, as long as those variables affect the treatment in a relatively linear manner. Defining the treatment to include such variables as $T_{A-L}(X,Y)$, that treatment can be defined according to:

$$T_{A-L}(X, Y) = \left[\frac{T_{A-T}(X, Y)}{\eta \cdot \kappa_{(X,Y)}} \cdot \sum_{n=1}^{N} W_n(\xi_n)\right] - \sum_k P_k(X, Y) \quad \text{[Eq. 49]}$$

where $W_n$ represents the magnitude of the weighting term associated with the variable, the symbol $\eta$ represents material properties, $\kappa_{(X,Y)}$ represents an ablation efficiency compensation function, and $$\sum_k P_k(X, Y)$$

represents other spatially-dependent, predictable processes. Here, can represent various factors, such as, for example, photopic pupil diameter, mesopic pupil diameter, cycloplegic pupil diameter, near-vision preoperative refraction sphere, near-vision preoperative refraction cylinder, near-vision preoperative refraction axis, far-vision preoperative refraction sphere, far-vision preoperative refraction cylinder, far-vision preoperative refraction axis, near-vision postoperative refraction sphere, near-vision postoperative refraction cylinder, near-vision postoperative refraction axis, far-vision postoperative refraction sphere, far-vision postoperative refraction cylinder, far-vision postoperative refraction axis, left eye, right eye, asphericity, axis angle, optical zone diameter, transition zone diameter, central pachymetry, corneal topographic measurements, spherical aberration as a percent of total root-mean-square (RMS) aberration, coma as a percent of total RMS aberration, trefoil as a percent of total RMS aberration, high-order aberrations as a percent of total RMS aberration, astigmatism index, corneal width, front surface corneal curvature, back surface corneal curvature, front-to-back alignment, age, side of dominant eye, preference between day vision and night vision, treatment purpose, ethnicity, iris color, gender, temperature, humidity, microkeratome used for corneal resection, flap size, time elapsed from opening of flap to ablation, surgeon, estimated total time during opening of flap, expected flap thickness, procedure type, scanner used, laser used, day of surgery, location of flap hinge, or any combination of these variables, which are also referred to herein as confounding parameters. The coefficients of Eq. 49 can be determined by known statistical methods, so long as neuro-ocular wavefront data from a sufficient population of subjects has been gathered. Such data can be obtained, for some embodiments, in accordance with one or more of the processes set forth in FIGS. 17 through 27B, below.

For some embodiments, the ablation efficiency function $\kappa_{(X,Y)}$ accounts for the loss of ablation efficiency across the cornea surface. For those embodiments, the reflectance $R_{unp}$ of the corneal surface is calculated as:

$$R_{unp} = \frac{|r_p|^2 + |r_s|^2}{2} \quad \text{[Eq. 50]}$$

where:

$$r_p = \frac{\tilde{n}_2 \cos\theta_1 - n_1 \cos\theta_2}{\tilde{n}_2 \cos\theta_1 + n_1 \cos\theta_2} \quad \text{[Eq. 51]}$$

and:

$$r_s = \frac{n_1 \cos\theta_1 - \tilde{n}_2 \cos\theta_2}{n_1 \cos\theta_1 + \tilde{n}_2 \cos\theta_2} \quad \text{[Eq. 52]}$$

with $\tilde{n}_2$ representing a complex index of refraction for corneal tissue, $n_1$ representing a complex index of refraction for incident medium, $\theta_1$ representing an incident angle, and $\theta_2$ representing an internal angle refracted according to Snell's law. The incident angle is calculated from corneal topographic data, Z, at point (X,Y) in accordance with:

$$\cos\theta_1 = \frac{\nabla Z \cdot \hat{z}}{|\nabla Z|} \quad \text{[Eq. 53]}$$

thereby resulting in:

$$\tan\theta_1 = \sqrt{\left(\frac{\partial Z}{\partial R}\right)^2 + \left(\frac{1}{R} \cdot \frac{\partial Z}{\partial \varphi}\right)^2} \quad \text{[Eq. 54]}$$

where R is the distance from the corneal vertex to the point of interest (calculated as $R = \sqrt{X^2 + Y^2}$), and $\varphi$ is the azimuthal angle such that $$\tan\varphi = \frac{Y}{X}.$$

If the cornea is represented by a conic section of:

$$X^2+Y^2+Z^2(1+K)-2ZR_0=0 \quad [\text{Eq. 55}]$$

where K is a conic constant, and $R_0$ is a paraxial radius of curvature, then:

$$\tan\theta_1 = \frac{\frac{R}{R_0}}{\sqrt{1-(1+K)\cdot\frac{R^2}{R_0^2}}} \quad [\text{Eq. 56}]$$

From Eq. 54 or Eq. 56, in conjunction with Eqs. 51 through 52, the ablation depth can be calculated according to:

$$d = d_0 \cdot \log_e\left[\frac{\phi}{\phi_0}\right] \quad [\text{Eq. 57}]$$

where $d_0$ is the ablation depth when $\phi=e\cdot\phi_0$ or $\phi=2.718\cdot\phi_0$, $\phi$ is the applied fluence, and $\phi_0$ is the ablation threshold. Thus, for a small beam ablation where the laser bean width is much smaller than the pupil diameter, Eq. 57 can be rewritten as:

$$d = d_0 \cdot \log_e\left[\frac{\phi}{\phi_0}\cdot(1-R_{unp})\cdot\cos\theta_1\right] \quad [\text{Eq. 58}]$$

Given this, a rudimentary approximation of the ablation efficiency can be represented according to:

$$\kappa_{(X,Y)} = \frac{d(X,Y)}{d(0,0)} = \frac{\log_e\left[\frac{\phi}{\phi_0}\cdot(1-R_{unp})\cdot\cos\theta_1\right]}{\log_e\left[\frac{\phi}{\phi_0}\cdot\left(1-R_{unp(X=0,Y=0)}\right)\right]}. \quad [\text{Eq. 59}]$$

If treatment is applied in N layers, then the transition zone treatment can be represented as:

$$T_{A-T}(X,Y) = \sum_{1}^{N_L(X,Y)} t_i(X,Y) \quad [\text{Eq. 60}]$$

where $N_L(X,Y)$ represents the number of layers at point (X,Y), and:

$$t_i(X,Y) = t_{layer} \cdot \frac{d(X,Y)}{d(0,0)} \quad [\text{Eq. 61}]$$

$$= t_{layer} \cdot \frac{\log_e\left[\frac{\phi}{\phi_0}\cdot(1-R_{i,unp})\cdot\cos\theta_{i,1}\right]}{\log_e\left[\frac{\phi}{\phi_0}\cdot\left(1-R_{unp(X=0,Y=0)}\right)\right]}$$

with $t_{layer}$ being a nominal value for the removal rate and $t_i(X,Y)$ being the actual material removed per layer at that point. If treatment is presumed to be constant across the pupil plane, then:

$$N_0(X,Y) = \frac{T_{A-T}(X,Y)}{t_{layer}} \quad [\text{Eq. 62}]$$

Thus, according to Eqs. 60 and 62:

$$\kappa_{(X,Y)} = \frac{N_0(X,Y)}{N_L(X,Y)}. \quad [\text{Eq. 63}]$$

Figure 11:
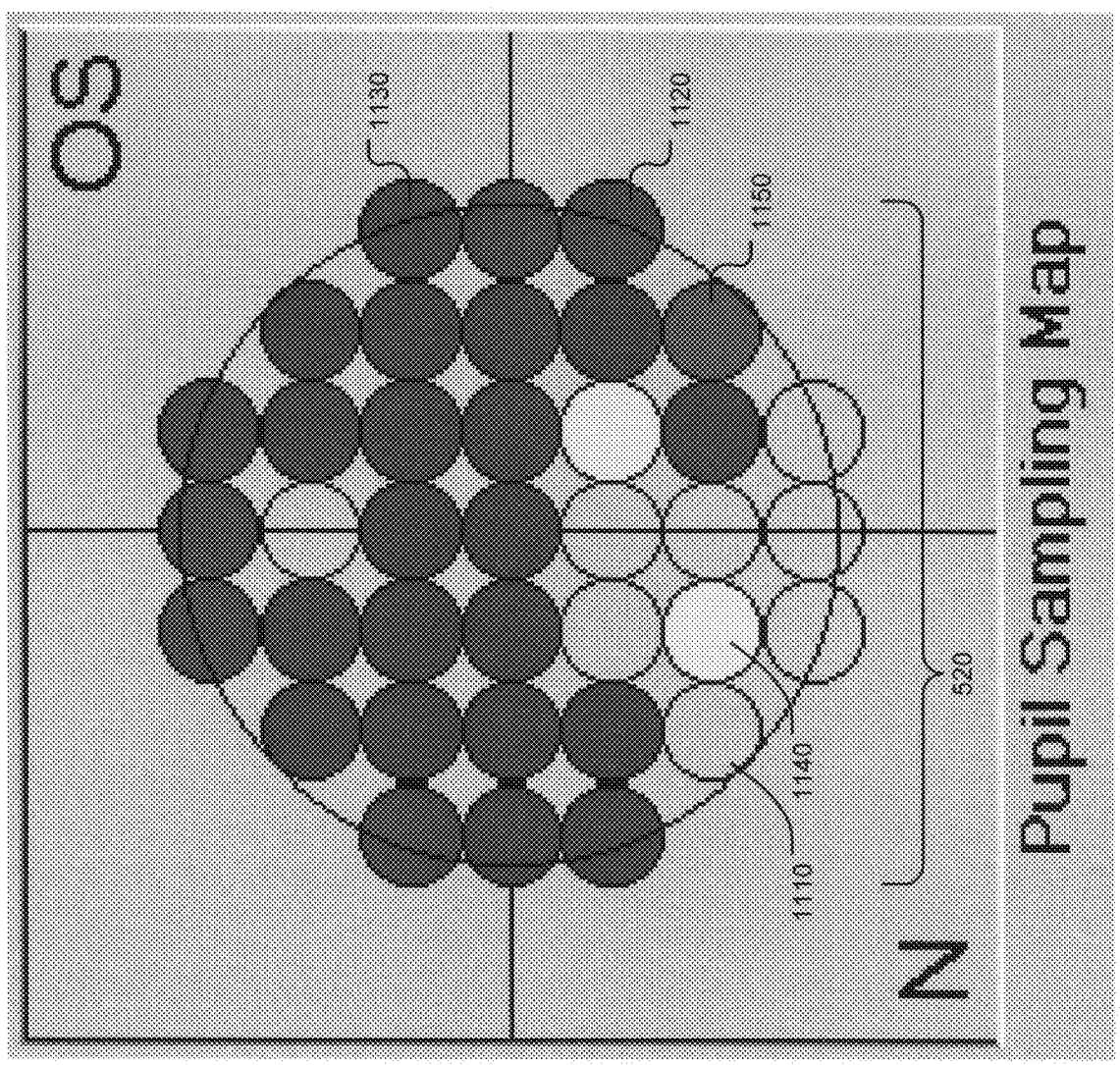
FIG. 11 is a diagram showing an embodiment of a sampling map that has a predefined matrix of sampling points.

FIG. 11 is a diagram showing an embodiment of a sampling map that has a predefined matrix of sampling points. Specifically, FIG. 11 shows a nominal sampling map 520 in which the pupil has been divided into a predefined matrix of sampling points. Each sampling point represents a visual test zone. The sampling points are shown in FIG. 11 as the small circles of various colors. The embodiment of FIG. 11 shows a sampling from a subject at a particular stage in the data-acquisition process. Specifically, the blank circles 1110 represent those visual zones that have not yet been sampled. The yellow circles 1140 represent those visual zones that have been temporarily skipped and which may be sampled at a later time. These temporarily-skipped zones can be skipped as a result of the operator choosing to conduct the data acquisition out of order, or, alternatively, these zones can be temporarily skipped due to feedback from the subject that indicates difficulty in providing input. The dark blue circles 1130 represent those visual zones for which the subject has provided input. The red circles 1120 represent those visual zones that have been permanently skipped due to difficulty in obtaining a reliable reading from the subject. The light blue circle 1150 represents the visual zone for which data is currently being obtained. As one can imagine, neuro-ocular wavefront data can be estimated by obtaining input from the subject for each of the visual zones.

Figure 12:
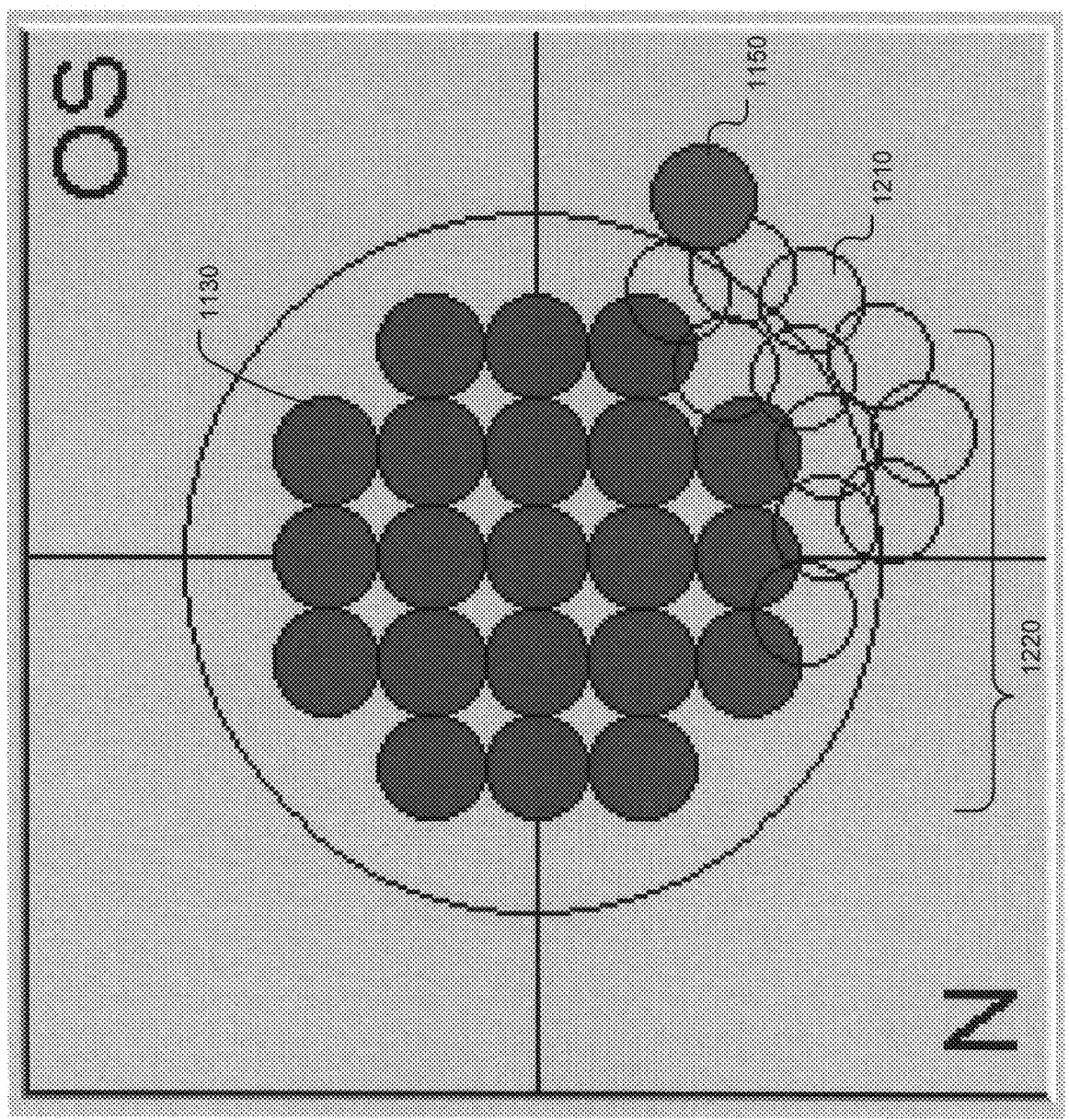
FIG. 12 is a diagram showing an embodiment of a sampling map that permits customization of sampling points.

FIG. 12 is a diagram showing an embodiment of a sampling map that permits customization of sampling points. For some embodiments, it may be desirable to obtain data from various visual zones that do not easily coincide with the predefined sampling map of FIG. 11. For those embodiments, a customized sampling map 1220 can be used in which predefined sampled visual zones 1130 can be supplemented with custom sample points 1210. By permitting customization of the sampling map, more accurate neuro-ocular waveform data can be obtained.

Figure 13:
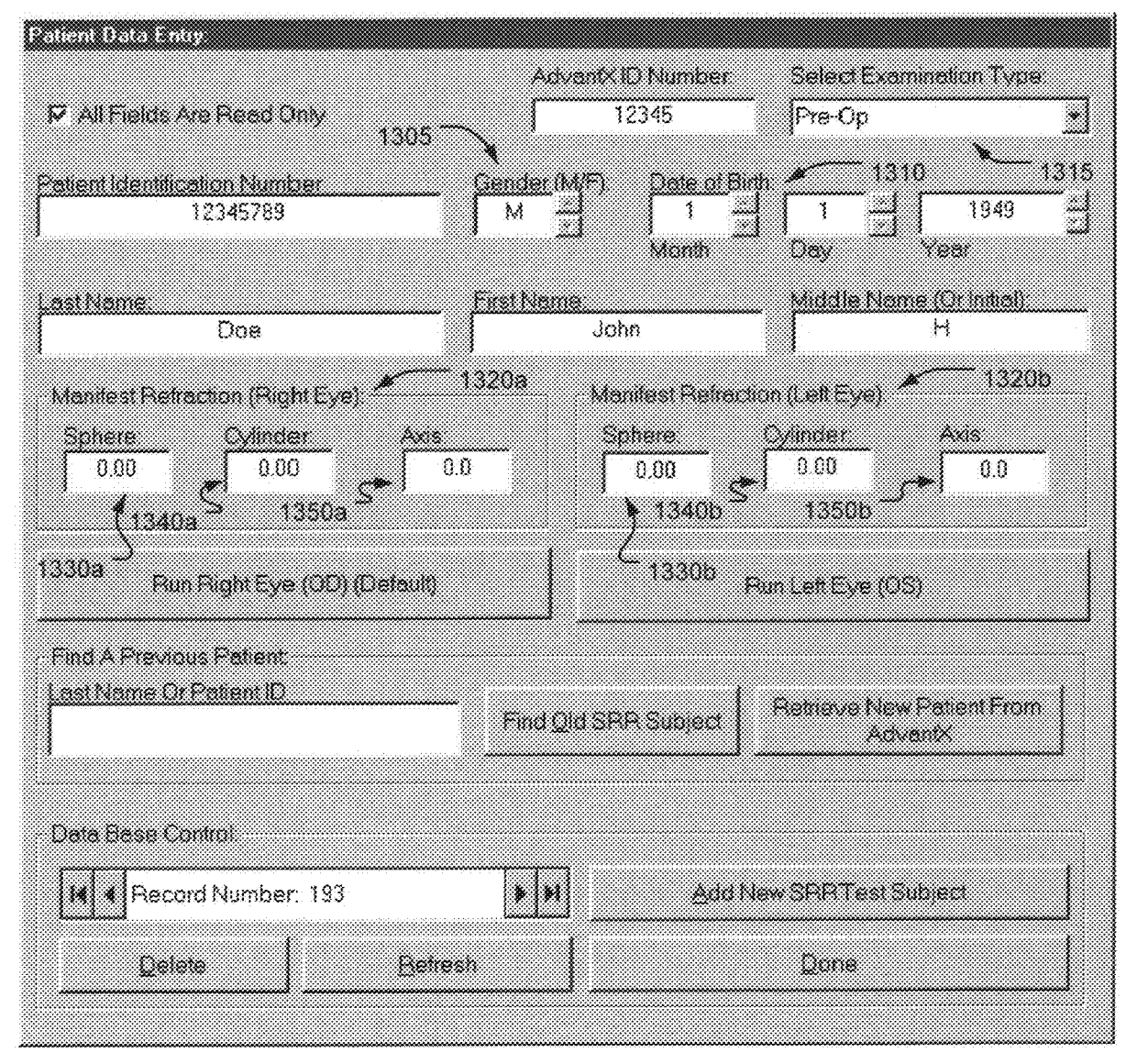

FIG. 13 is a diagram showing an embodiment of a subject data entry screen for a refractometer adapted to acquire neuro-ocular wavefront data. As described above, in some embodiments, subject information can be used to statistically compute various subject-related or environment-related factors that may affect treatment. FIG. 13 shows an embodiment of a data entry screen by which the subject data can be provided. As shown in FIG. 13, the data entry screen comprises an input 1305 for the gender of the subject, an input 1310 for the date of birth of the subject, an input 1315 for the type of examination, and inputs 1320a, 1320b (collectively referred to herein as 1320) for optical characteristics for each eye. The optical characteristics, in some embodiments, can include the sphere 1330a, 1330b, the cylinder 1340a, 1340b, and the axis 1350a, 1350b for each eye. It should be appreciated that the data entry screen can be customized, as a matter of design, to include other fields and, also, to omit certain fields.

Figure 14:
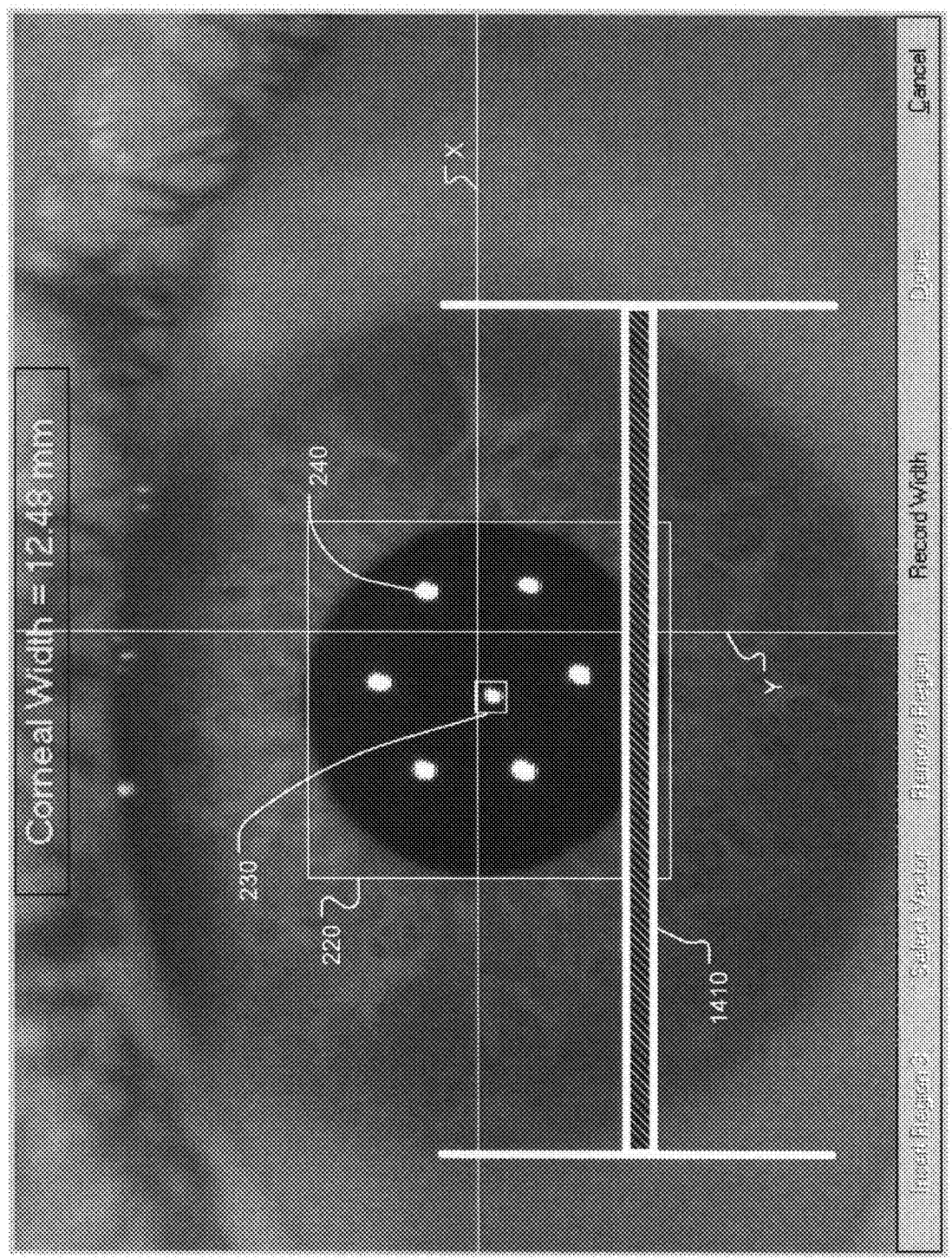
FIG. 14 is a diagram showing an embodiment of a video display that facilitates on-screen measurements of physical characteristics of the eye.

FIG. 14 is a diagram showing an embodiment of a video display that facilitates on-screen measurements of physical characteristics of the eye. Specifically, FIG. 14 shows, with reference to the x-axis and the y-axis, the pupil tracking box 220 and the Purkinje location 230 as well as the eye illumination LED locations 240. The embodiment of FIG. 14 includes an on-screen measurement tool 1410 that can be adjusted with a cursor (not shown) using a graphical user interface (GUI, not shown). The on-screen measurement tool 1410, for some embodiments, can measure the width of the cornea. It should be appreciated that the system can be configured to accommodate other similar measurements.

Figure 15:
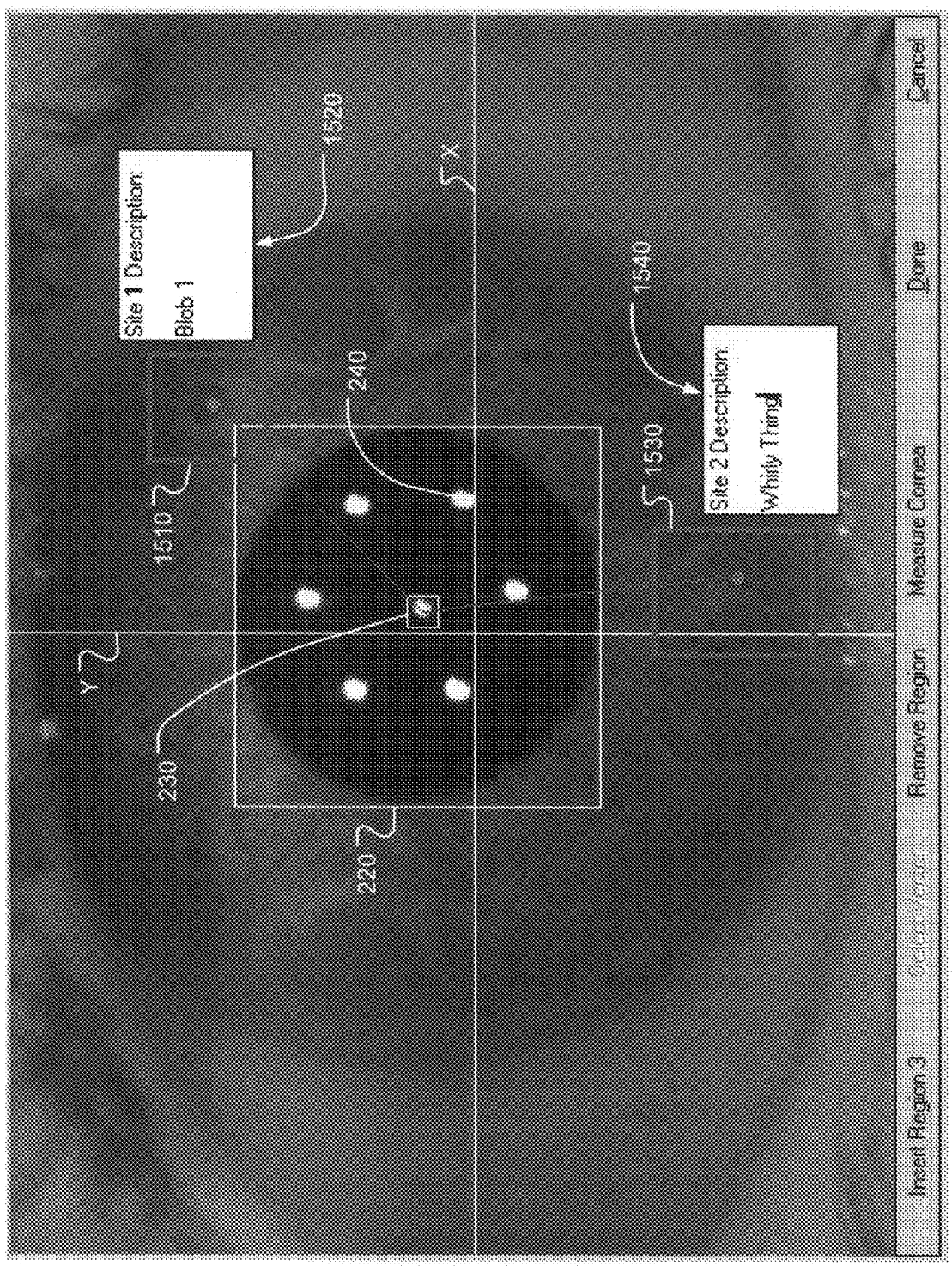
FIG. 15 is a diagram showing an embodiment of a video display that permits annotation of various features of the eye.

FIG. 15 is a diagram showing an embodiment of a video display that permits annotation of various features of the eye. For this embodiment, various features 1510, 1530 can be selected with a cursor (not shown) using a GUI (not shown). The selected features 1510, 1530 can be annotated 1520, 1540 in order to provide more information on the characteristics of the eye. This information can subsequently be used to refine the diagnosis and treatment of vision.

As one can see from FIGS. 14 and 15, the aberrometer that determines the neuro-ocular wavefront error can be configured in a variety of ways, thereby permitting greater accuracy in diagnosing and treating the visual system of a subject.

Figure 16:
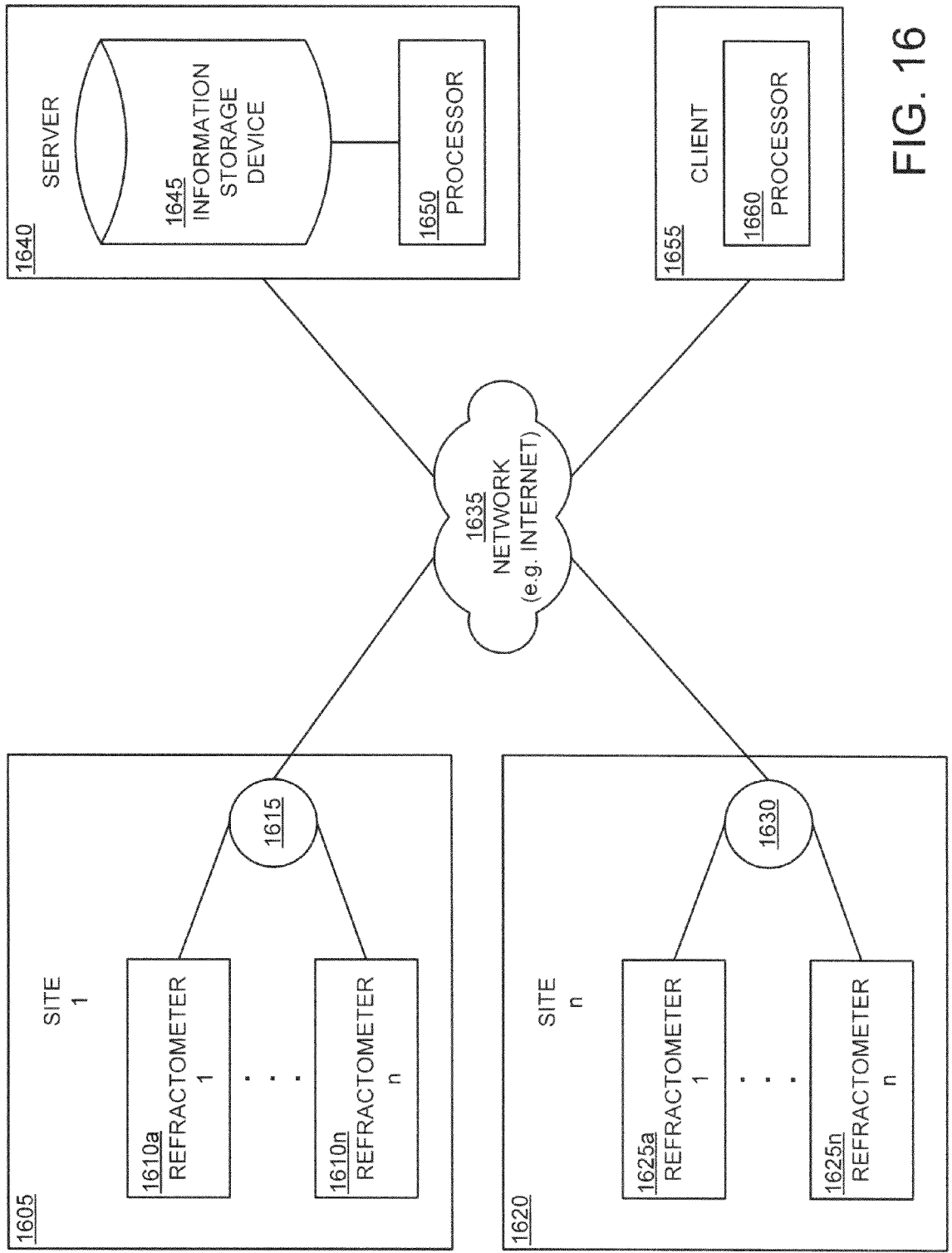
FIG. 16 is a block diagram showing an embodiment of a system configured to aggregate data from multiple refractometers.

FIG. 16 is a block diagram showing an embodiment of a system configured to aggregate data from multiple spatially resolved refractometers. As noted with reference to Eq. 49, statistical analysis can be performed on neuro-ocular wavefront data. The embodiment of FIG. 16 provides one example, among others, of a system that is configured to obtain multiple sets of neuro-ocular wavefront data.

As shown in FIG. 16, in some embodiments, multiple clinical sites 1605, 1620 are communicatively coupled to a server 1640 over a network 1635, such as, for example, the Internet. FIG. 16 also shows a client 1655 that is communicatively coupled to the Internet 1635. Each clinical site 1605, 1620 can include multiple refractometers 1610a . . . 1610n (collectively 1610), 1625a . . . 1625n (collectively 1625) that are communicatively coupled to the Internet 1635 through routers 1615, 1630 that are located at their respective clinical sites 1605, 1620. Since networked environments are known in the art, further discussion of the routers 1615, 1630 and the Internet 1635 is omitted here.

The server 1640 is also communicatively coupled to the Internet 1635, thereby permitting data exchange between the server 1640 and the various refractometers 1610, 1625. The server 1640 comprises an information storage device 1645, such as, for example, a high-capacity hard drive or other non-volatile memory devices, which are known in the art. Coupled to the information storage device 1645 is a processor 1650. The processor 1650, for some embodiments, is configured to handle the incoming and outgoing data from the server 1640. Since such processor functions are known in the art, further discussion of those functions is omitted here. In addition to handling such known functions, the processor 1650 is also configured to respond to requests from the client 1655. Thus, for example, the server processor 1650 receives queries from the client processor 1660 and provides any requested service to the client 1655 in response to the query.

The client processor 1660 is configured to generate requests to the server 1640 and receive data in response to those queries. The client processor 1660 is further configured to perform statistical analysis on the requested data. Since those statistical processes, in addition to the hardware and software for performing the statistical analysis, are known in the art, further discussion of those processor functions is omitted here.

As shown in FIG. 16, both the server processor 1650 and the client processor 1660 can be configured, using various known software and hardware, to gather data, exchange data, and process data. Specifically, for some embodiments, the client processor can be appropriately configured to perform the mathematical operations as defined in Eqs. 1 through 63. In other words, the processors 1650, 1660 can be configured to generate the neuro-ocular wavefront error data using the inputs received from a subject. Additionally, the processors 1650, 1660 can be configured to calculate treatment profiles from the neuro-ocular wavefront data. For some embodiments, the processor 1650 includes various logic components that are adapted to execute the processes described with reference to FIGS. 17 through 27B. Those processes can be embodied in a neuro-ocular wavefront program, which computes the neuro-ocular wavefront data from the inputs provided by the subject, and statistical regression program, which computes the effect of various vision parameters on the neuro-ocular wavefront data.

As one can see, by having such a distributed system in which data is stored at a central repository 1645, multiple sets of neuro-ocular wavefront data can be aggregated to better estimate various effects, such as, for example, subject effects, environmental effects, and optical effects.

Having described various embodiments of systems associated with the acquisition and analysis of neuro-ocular wavefront data, attention is turned to FIGS. 17 through 27B, which show various processes associated with neuro-ocular wavefront data acquisition and analysis. It should be appreciated that the following processes, in some embodiments, can be executed by the above-described systems. Alternatively, the processes of FIGS. 17 through 27B can also be executed with other devices that are configured appropriately.

In a broad sense, the processes of FIGS. 17 through 27B can be seen as an interactive process in which a subject (or patient) provides neuro-ocular wavefront data by interacting with a spatially-resolved refractometer. For example, in some embodiments, the subject is placed in front of a refractometer, and an eye-tracking algorithm tracks the location of the subject's pupil in order to eliminate much of the movement artifacts that may be present due to natural eye movements. The eye, and more specifically the pupil, is divided into multiple zones. For some embodiments, those zones are defined by a matrix of sampling points, which can be predefined sampling points or customized sampling points. The refractive characteristic of each zone is obtained interactively from the subject. Since that information is obtained with feedback from the subject, the obtained data includes neuro-ocular information, rather than merely ocular information. Once those characteristics of all of the zones have been obtained, a neuro-ocular wavefront can be estimated from those discreet sampling points. As noted above, due to the input by the subject, the neuro-ocular wavefront data provides some information on the neuro-ocular pathways, rather than merely providing information from the eye alone.

Figure 17:
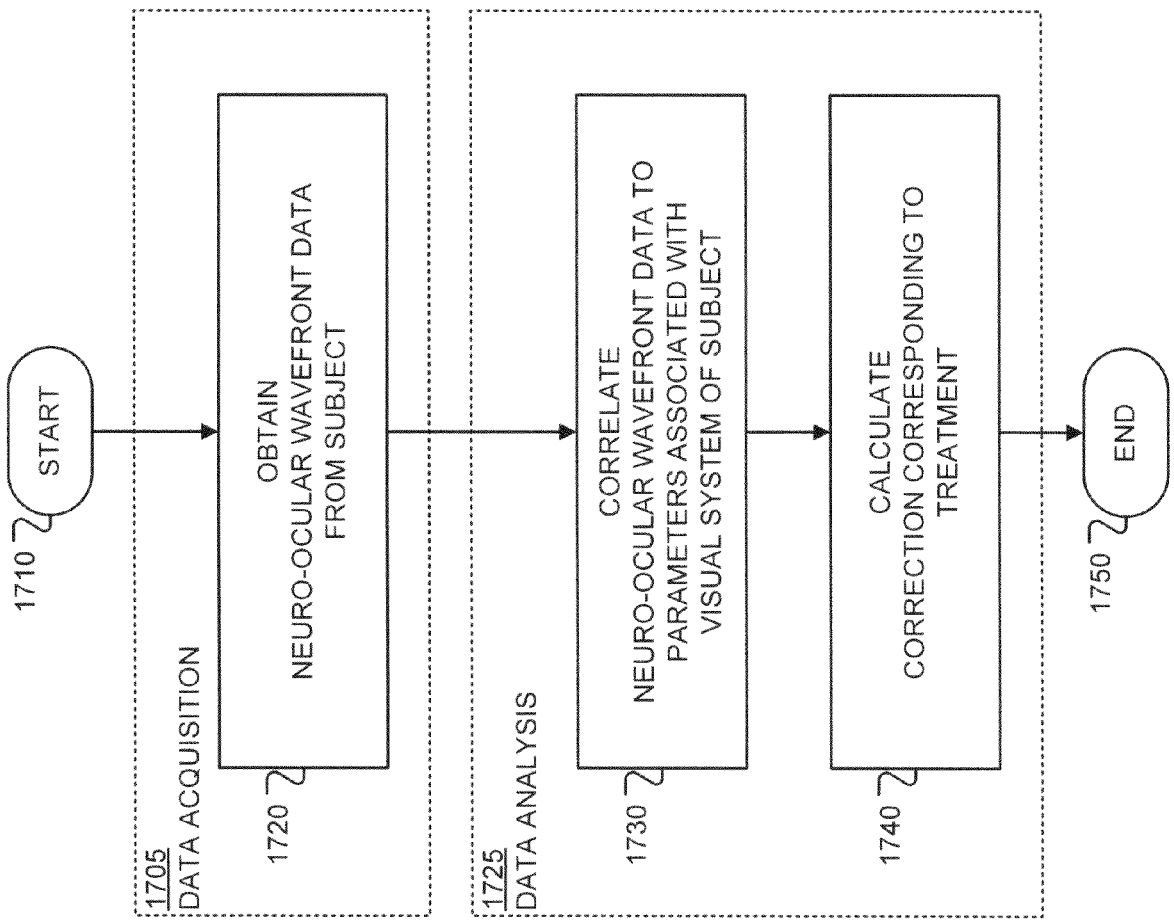
FIG. 17 is a flowchart showing an embodiment of a method for acquiring and processing neuro-ocular wavefront data.

FIG. 17 is a flowchart showing an embodiment of a method for acquiring and processing neuro-ocular wavefront data. As shown in FIG. 17, some embodiments of the process can be broadly seen as comprising two steps. First, a data acquisition step (1705) and a data analysis step (1725). For some embodiments, the data acquisition step (1705) comprises the step of obtaining (1720) neuro-ocular wavefront data from a subject, while the data analysis step (1725) comprises the step of ascertaining characteristics of a visual system from the obtained neuro-ocular wavefront data. The neuro-ocular wavefront data can be obtained (1720), in some embodiments, using one or more of the systems described with reference to FIGS. 1 through 16.

In other embodiments, the data analysis step (1725) comprises the step of correlating (1730) neuro-ocular wavefront data to parameters associated with the visual system of the subject. The parameter associated with the visual system can be, but is not limited to, an optical parameter, a subject parameter, or an environment parameter. The optical parameter, the subject parameter, and the environmental parameter, in the aggregate, are referred to herein as "vision parameters." In some embodiments, the optical parameters can include, but are not limited to, photopic pupil diameter, mesopic pupil diameter, cycloplegic pupil diameter, near-vision preoperative refraction sphere, near-vision preoperative refraction cylinder, near-vision preoperative refraction axis, far-vision preoperative refraction sphere, far-vision preoperative refraction cylinder, far-vision preoperative refraction axis, near-vision postoperative refraction sphere, near-vision postoperative refraction cylinder, near-vision postoperative refraction axis, far-vision postoperative refraction sphere, far-vision postoperative refraction cylinder, far-vision postoperative refraction axis, left eye, right eye, asphericity, axis angle, optical zone diameter, transition zone diameter, central pachymetry, spherical aberration as a percent of total root-mean-square (RMS) aberration, coma as a percent of total RMS aberration, trefoil as a percent of total RMS aberration, high-order aberrations as a percent of total RMS aberration, astigmatism index, corneal width, front surface corneal curvature, back surface corneal curvature, front-to-back alignment, or any combination of these optical parameters.

The subject parameters, in some embodiments, can include, but are not limited to, age, side of dominant eye, preference between day vision and night vision, treatment purpose, ethnicity, iris color, gender, or any combination of these subject parameters.

For some embodiments, the environmental parameters can include, but are not limited to, temperature, humidity, microkeratome used for corneal resection, flap size, time elapsed from opening of flap to ablation, surgeon, estimated total time during opening of flap, expected flap thickness, procedure type, scanner used, laser used, day of surgery, location of flap hinge, or any combination of these environmental parameters.

Thereafter, the data analysis step (1725) proceeds to calculate (1740) a correction corresponding to one or more treatments for reducing the anomalies in a visual system of the subject. The calculation of the correction can be seen as a calculation of one or more correction factors. Thus, the correction can correspond to a prescription for spectacles. In other embodiments, the correction can correspond to a prescription for contact lenses. However, in a preferred embodiment, the correction can correspond to a treatment for a refractive surgical technique, such as, but not limited to, radial keratotomy (RK), astigmatic keratotomy (AK), automated lamellar keratoplasty (ALK), photorefractive keratectomy (PRK), laser in situ keratomileusis (LASIK), intracorneal ring segments (Intacs), intracorneal lens insertion, laser thermal keratoplasty (LTK), phakic intraocular lenses, or any combination of these refractive surgical techniques. Likewise, the correction factors can correspond to one or more factors that affect an ablation profile for a corresponding refractive surgical method.

Figure 18:
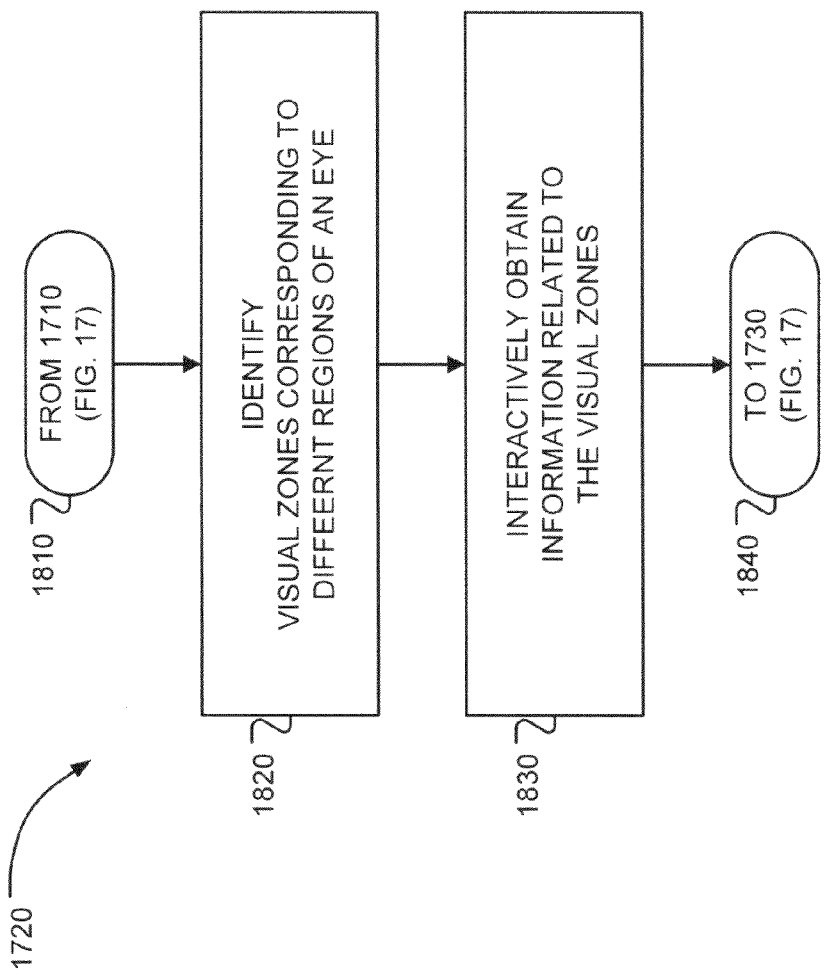
FIG. 18 is a flowchart showing, in greater detail, an embodiment of the data-acquisition step from FIG. 17.

FIG. 18 is a flowchart showing, in greater detail, an embodiment of the data-acquisition step (1720) from FIG. 17. As shown in FIG. 18, the step of obtaining (1720) the neuro-ocular wavefront data can be seen, for some embodiments, as a two-step process. In the first step, the process identifies (1820) visual zones corresponding to different regions of the eye. Thereafter, the process interactively obtains (1830) information related to the visual zones. The information can be obtained using an interactive refractometer, such as, for example, one or more refractometers that have been described with reference to FIGS. 1 through 16.

Figure 19:
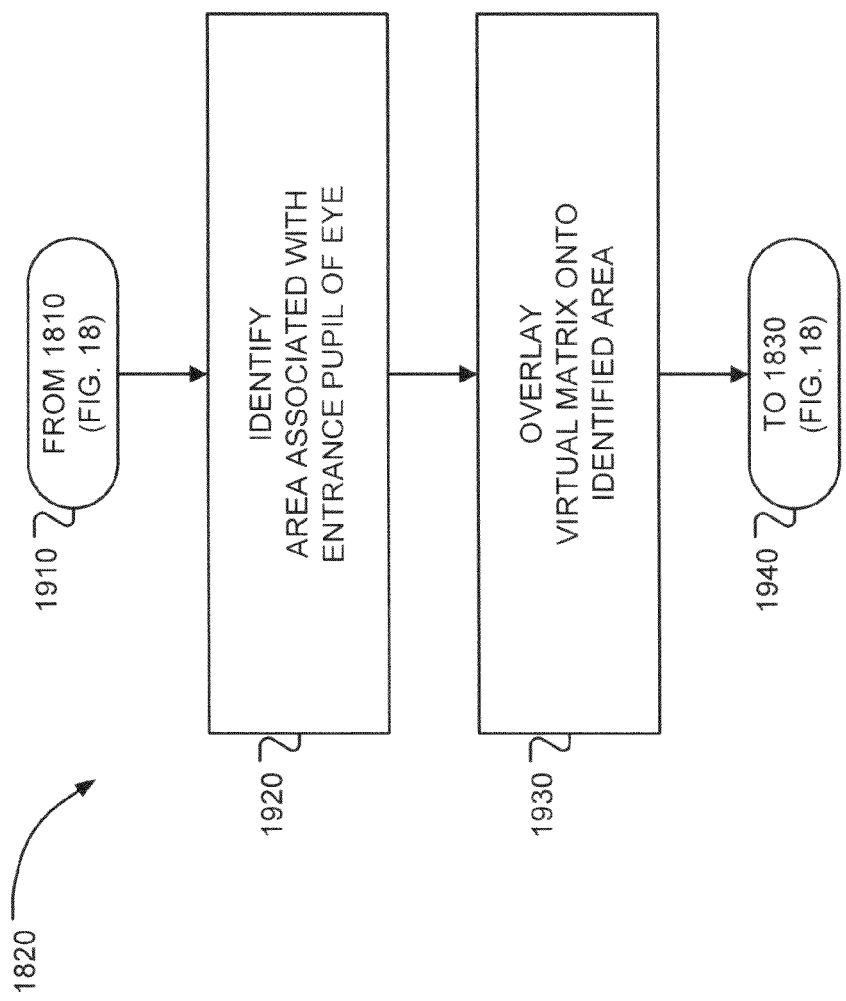
FIG. 19 is a flowchart showing, in greater detail, an embodiment of the step of identifying visual zones, from FIG. 18.

FIG. 19 is a flowchart showing, in greater detail, an embodiment of the step of identifying (1820) visual zones, from FIG. 18. As shown in FIG. 19, in some embodiments, the process identifies (1920) an area associated with the entrance pupil of the eye. Thereafter, the process overlays (1930) a virtual matrix onto the identified area. Preferably, the area associated with the entrance pupil of the eye is identified and tracked using the Purkinje method, as described above. Thus, when the virtual matrix is overlayed (1930) onto the pupil area, that matrix will be in substantially the same place, regardless of spurious eye movements.

Figure 20A:
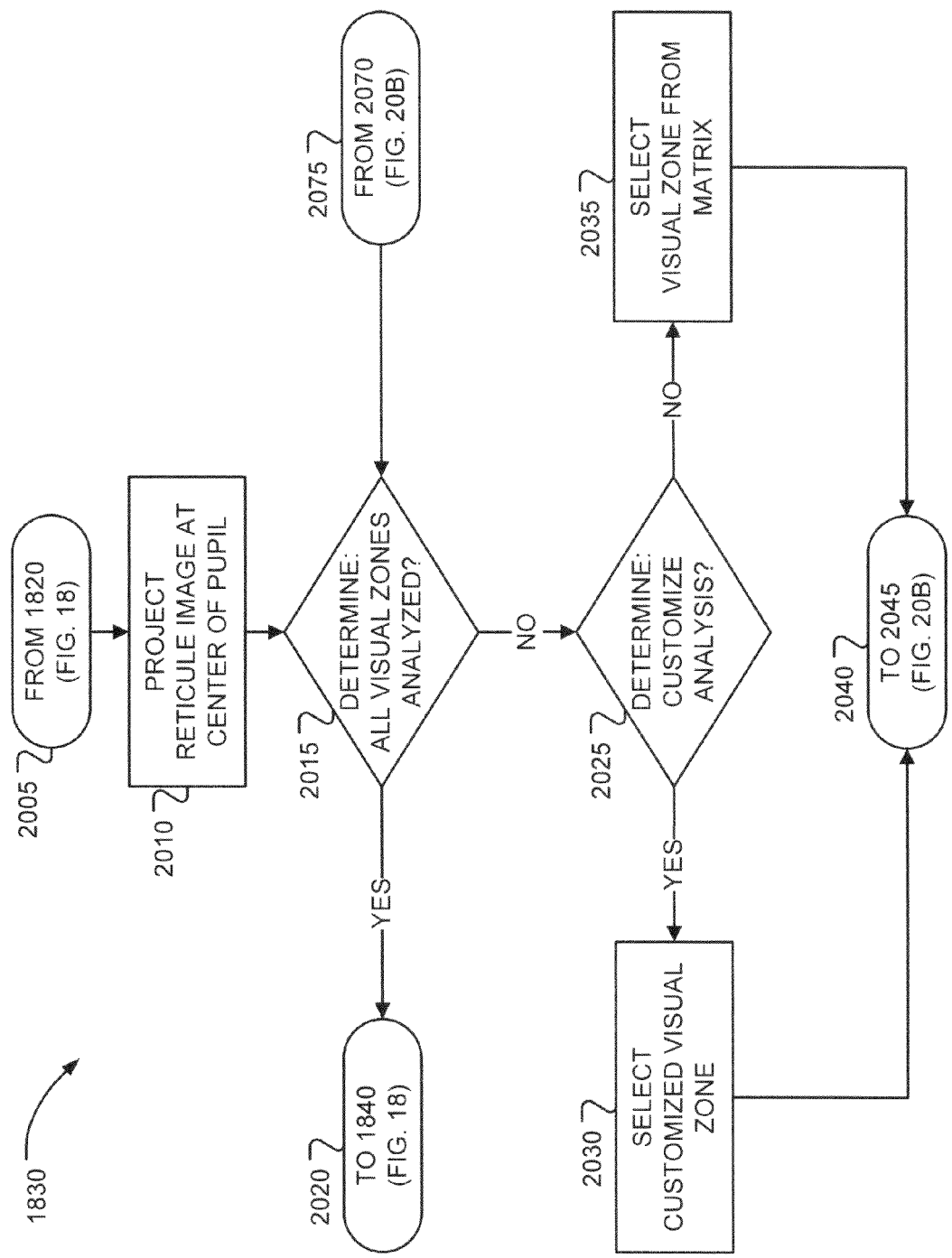
FIGS. 20A and 20B are flowcharts showing, in greater detail, an embodiment of the step of interactively obtaining information, from FIG. 18.
Figure 20B:
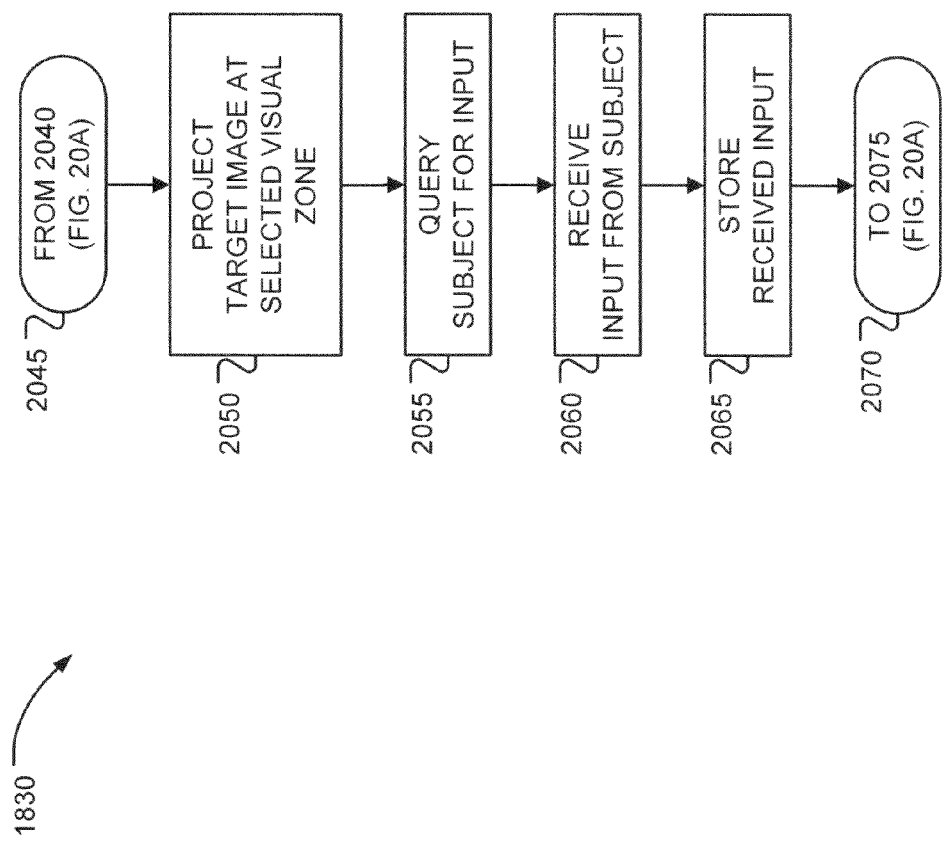

FIGS. 20A and 20B are flowcharts showing, in greater detail, an embodiment of the step of interactively obtaining (1830) information, from FIG. 18. As shown in FIG. 20A, an embodiment of the process begins (2005) when a reticule image is projected (2010) at the center of the eye and data is gathered from the various sampling points or visual zones. In that regard, the process determines (2015) whether or not all visual zones have been analyzed and, so long as all of the visual zones have not been analyzed, further determines (2025) whether or not a customized sampling map should be used for the analysis. If the process determines (2025) that the analysis is customized, then the next customized visual zone is selected (2030). For some embodiments, this can be done interactively with the operator of the refractometer through a graphical user interface (GUI) similar to that shown in FIG. 12. If, on the other hand, the process determines (2025) that the analysis is not customized, then the next visual zone is selected (2035) from a predefined matrix. In some embodiments, the predefined matrix can be configured similar to the matrix shown in FIG. 11. Regardless of whether a predefined visual zone is selected (2035) or a customized visual zone is selected (2030), the process continues to FIG. 20B.

As shown in FIG. 20B, a target image is projected (2050) at the selected visual zone. Upon projecting the target image, the subject is queried (2055) for input, and that input is received (2060) from the subject. In some embodiments, the query can be configured as a display having an alignment target and a test spot, similar to the display shown in FIG. 8. The input from the subject can be received, for some embodiments, using a joystick or other input mechanism that permits the subject to align the test spot with the alignment target. Upon receiving (2060) the input from the subject, the received input is then stored (2065), and the process returns to FIG. 20A to determine (2015) whether or not all visual zones have been analyzed. In the event that all visual zones have been analyzed, the process exits (2020).

A blur image (also referred to herein as a blur anatomy) is one possible representation of image quality of human vision, insofar as the blur image has the following characteristics. First, the blur image plainly describes something that is representative of the quality of a subject's vision, and it is something that the subject can relate to in simple terms. Second, it provides some figure of merit that can be optimized using the parameters that are available to a surgeon as control variables. Also, there is a high degree of correlation between the simulation of the optimized condition and the actual experience of the patient when treated with the same conditions.

The blur image depicts a composite image perceived by the patient viewing a point source at an infinite distance, such as a bright star or a street light at a great distance. In one particular embodiment, the pupil is divided into three circular zones having outer diameters of approximately 3.65 mm, 5.16 mm, and 6.32 mm. Rays from an object are traced through the pupil and then to the image plane where they are color coded according to the pupillary zone through which they pass. Note that the image plane is determined with spatially resolved refractometry by localizing the patient preferred retinal plane and taking into account the effects of neural processing. This depiction provides a simultaneous estimate of vision quality for three different pupil diameters. The blur anatomy diagnostic is very similar to a conventional "spot diagram" used in optical system engineering, with the exception that the color coding provides additional information for different pupil diameters.

The location where a ray is incident on the retina can be calculated from the wavefront error using:

$$\alpha(x, y) = +\frac{\partial W}{\partial x} \qquad [\text{Eq. 64}]$$

and:

$$\beta(x, y) = -\frac{\partial W}{\partial y} \qquad [\text{Eq. 65}]$$

where x, and y are the horizontal and vertical coordinates in the entrance pupil plane. In this formulation, the coordinate position actually represents the perceived location of the ray in object space. Thus, Eqs. 64 and 64 are measured in radians or milliradians.

Once the plurality of points in the blur anatomy is calculated using Eqs. 64 and 65, the root-mean-square (RMS) blur radius of the blur pattern can be calculated using a standard statistical method. The first step in performing this calculation is to determine the coordinates of the blur centroid as:

$$\overline{\alpha} = \frac{\sum_i \alpha_i}{N} \qquad [\text{Eq. 66}]$$

and:

$$\overline{\beta} = \frac{\sum_i \beta_i}{N} \qquad [\text{Eq. 67}]$$

Once the coordinate of the centroid is determined, the calculation of RMS blur radius is completed according to:

$$\text{RMS blur radius} = \sqrt{\frac{\sum_i [(\alpha_i - \overline{\alpha})^2 + (\beta_i - \overline{\beta})^2]}{N}} \qquad [\text{Eq. 68}]$$

Corrections over the entire pupil are determined in the following manner. First the pupil is divided into several annular zones. Next, each of these zones is independently optimized using a conventional optimization algorithm. This calculation takes as inputs, the sphere, cylinder, and axis of a hypothetically-applied correction and determines the resultant RMS blur radius as an output figure of merit. The numerical optimization proceeds by finding the sphere, cylinder, and axis, that minimizes the RMS blur diameter using a representation according to:

$$\text{RMS blur radius} = f(\phi, \gamma, \theta) \qquad [\text{Eq. 69}]$$

These corrections relate to the neuro-ocular wavefront error in accordance with Eqs. 33 through 36.

In this embodiment of optimizing vision, there is variability associated with the method used to select the zone diameters. One embodiment of a method used to determine the zone diameters is denoted herein as the "equal area" method. This method endeavors to select the zone sizes by specifying that the contribution of each zone with relation to the image brightness should be equal for each zone. If the pupil diameter under pharmacological dilation is presumed to be the maximum pupil diameter possible, then the diameter of the $i^{th}$ zone, $D_i$, can be determined from the maximum pupil diameter, $D_{max}$, and the number of zones, N, using:

$$D_N = D_{max} \qquad [\text{Eq. 70}]$$

$$D_{N-1} = D_N \cdot \sqrt{\frac{N-1}{N}}$$

$$D_{N-2} = D_N \cdot \sqrt{\frac{N-2}{N}}$$

etc.

etc.

$$D_1 = D_N \cdot \sqrt{\frac{1}{N}}$$

Thus, for example, when N=3, the outer diameters of the three zones is:

$$D_3 = D_{max}, \qquad [\text{Eq. 71}]$$

$$D_2 = D_{max} \cdot \sqrt{\frac{2}{3}},$$

$$\text{and } D_1 = D_{max} \cdot \sqrt{\frac{1}{3}}.$$

One consequence of this approach to zone size selection is that the peripheral zones get progressively thinner. Besides having the effect of equalizing the intensity contribution of each zone, this method is also amenable for optimizing zone diameters of eyes with third-order spherical aberration. The reason being that, in this approach, zones designed according to Eq. 70 will become narrow at the same rate that the variation in sphere error increases. Therefore, each zone defined using this method will be treated with substantially the amount of spherical correction.

Another and more comprehensive method of selecting the zone diameters would be to utilize the same optimization technique used to optimize sphere, cylinder, and axis, except that zone diameter now becomes one of the variables as an input to the blur diameter calculation. In that optimization, a more complicated merit function can be designed, such that the average blur for each zone is quantified. This merit function may be designated "total vision blur," and for the case of three optical zones can be calculated according to:

$$\text{Total Vision Blur} = f(\phi_1, \gamma_1, \theta_1, 0, D_1) + f(\phi_2, \gamma_2, \theta_2, D_1, D_2) + f(\phi_3, \gamma_3, \theta_3, D_2, D_3) \qquad [\text{Eq. 72}].$$

The total vision blur represents the sum of the RMS blur for all three zones.

Although the optimization of this function containing twelve variables is considerably more complicated than each of the independent zone optimizations, such problems are relatively insignificant, given the available processing power.

In physiological optics, it is known that the outer or peripheral parts of the pupil contribute less to visual stimuli than do those from the central parts of the pupil. This effect, know as the Stiles Crawford effect, typically causes peripheral rays to contribute commensurately less to the perception of blur. This factor can be included in the calculation of RMS blur radius by modifying Eqs. 66 through 68 according to:

$$\bar{\alpha} = \frac{\sum_i \eta_i \cdot \alpha_i}{\sum_i \eta_i}$$ [Eq. 73]

$$\bar{\beta} = \frac{\sum_i \eta_i \cdot \beta_i}{\sum_i \eta_i}$$ [Eq. 74]

and:

$$\text{RMS blur radius} = \sqrt{\frac{\sum_i \eta_i \cdot [(\alpha_i - \bar{\alpha})^2 + (\beta_i - \bar{\beta})^2]}{\sum_i \eta_i}}.$$ [Eq. 75]

As before, the sum over i is carried out over all the points traced through the pupil from the object to the retina. As described above, such processes allows for computation of sphero-cylindrical corrections through blur optimization.

FIG. 21 is a flowchart showing, in greater detail, an embodiment of the step of correlating (1730) the neuro-ocular wavefront data to vision parameters, from FIG. 17. Specifically, FIG. 21 shows an embodiment in which the blur image is obtained. The blur image provides an emulation of the degree of blur that a subject sees without corrected vision. Additionally, depending on the parameters of interest, the blur image can also provide information of how a particular subject sees, should that subject's vision be corrected using various treatments. As shown in FIG. 21, the process begins by computing (2120) a pupil function from the neuro-ocular wavefront data. The pupil function can be calculated in accordance with:

$$P(x, y) = T(x, y) \cdot e^{i 2\pi \frac{W(x,y)}{\lambda}}, \quad \sqrt{x^2 + y^2} < \frac{D_{pupil}}{2}$$ [Eq. 76]

$$P(x, y) = 0, \quad \sqrt{x^2 + y^2} \geq \frac{D_{pupil}}{2}$$

where is the wavelength of incident light, $D_{pupil}$ is the diameter of the entrance pupil, and T(x,y) represents an apodizing function that can be used to model variations in effective pupillary transmission. For example, the Stiles-Crawford effect can be simulated according to:

$$T(x,y) = e^{-a(x^2+y^2)}$$ [Eq. 77]

with a being 0.16 (according to Stiles) or 0.105 (according to Moon and Spencer).

Upon computing (2120) the pupil function, a point-spread function (PSF) is obtained (2130) by Fourier transformation of the neuro-ocular wavefront data. The PSF can be computed according to:

$$I_{PSF}(\alpha,\beta) = C_0 \cdot |F(u,v)|_{u=\alpha/\lambda, v=\beta/\lambda}^2$$ [Eq. 78]

where (represents the angular position of a point in the farfield, F(u,v) is defined as the Fourier Transform of P(x,y), and $C_o$ is a constant.

A color image is resolved (2140) into its component color images (e.g., red, green, and blue images). Each of the component color images is convolved (2150) with the PSF, thereby generating component blurred images. The component blurred images are then combined to reconstruct (2160) the blur image. For some embodiments, the blur image can be generated by the processor 1660 of FIG. 16, so long as the processor is configured with the appropriate software and hardware to perform such a function. Since those having skill in the art should know how to appropriately configure the processor (e.g., write software code for a particular hardware platform), further discussion of such hardware and software is omitted here.

Figure 22A:
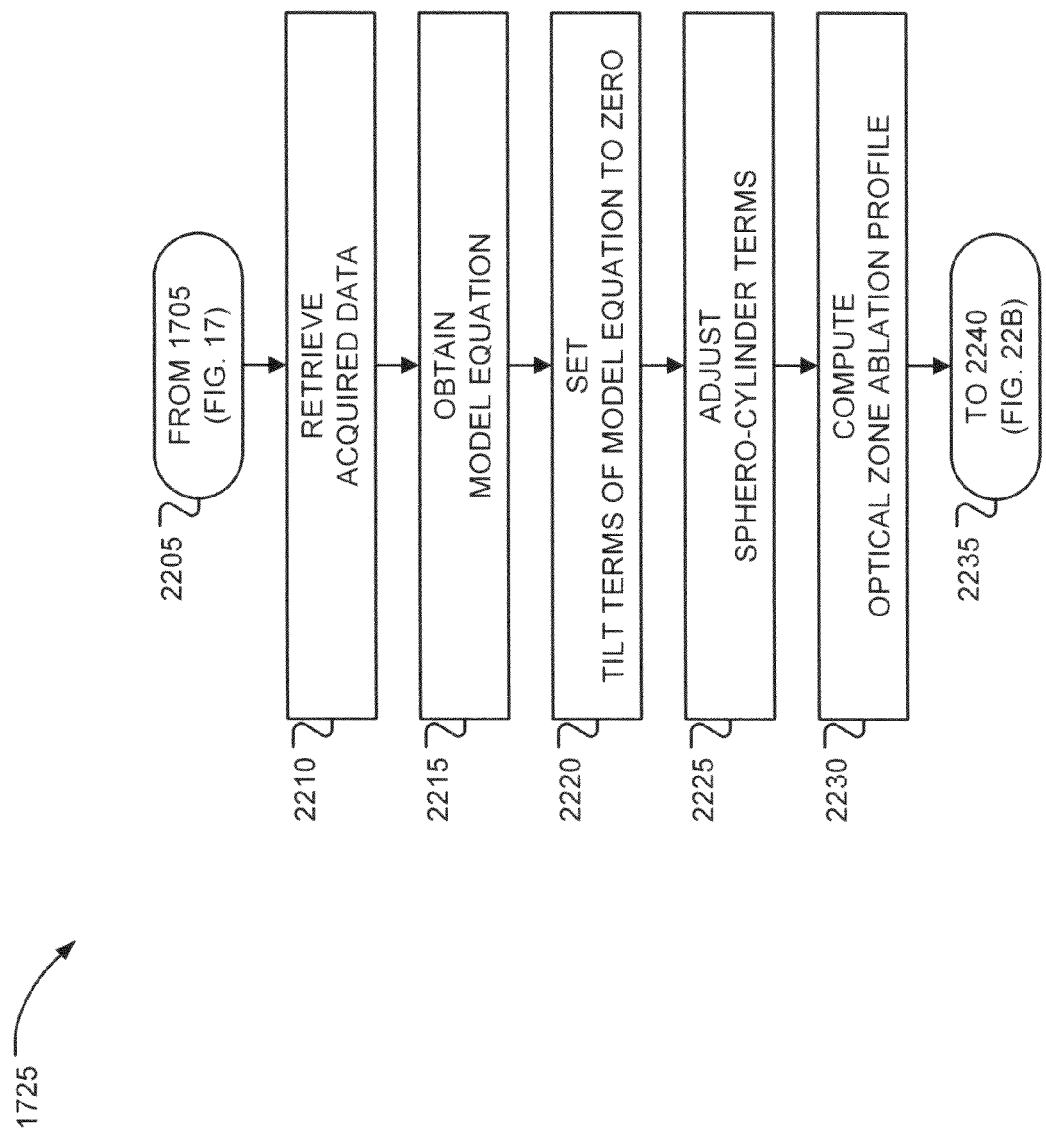
FIGS. 22A and 22B are flowcharts showing, in greater detail, an embodiment of the data-analysis step from FIG. 17.
Figure 22B:
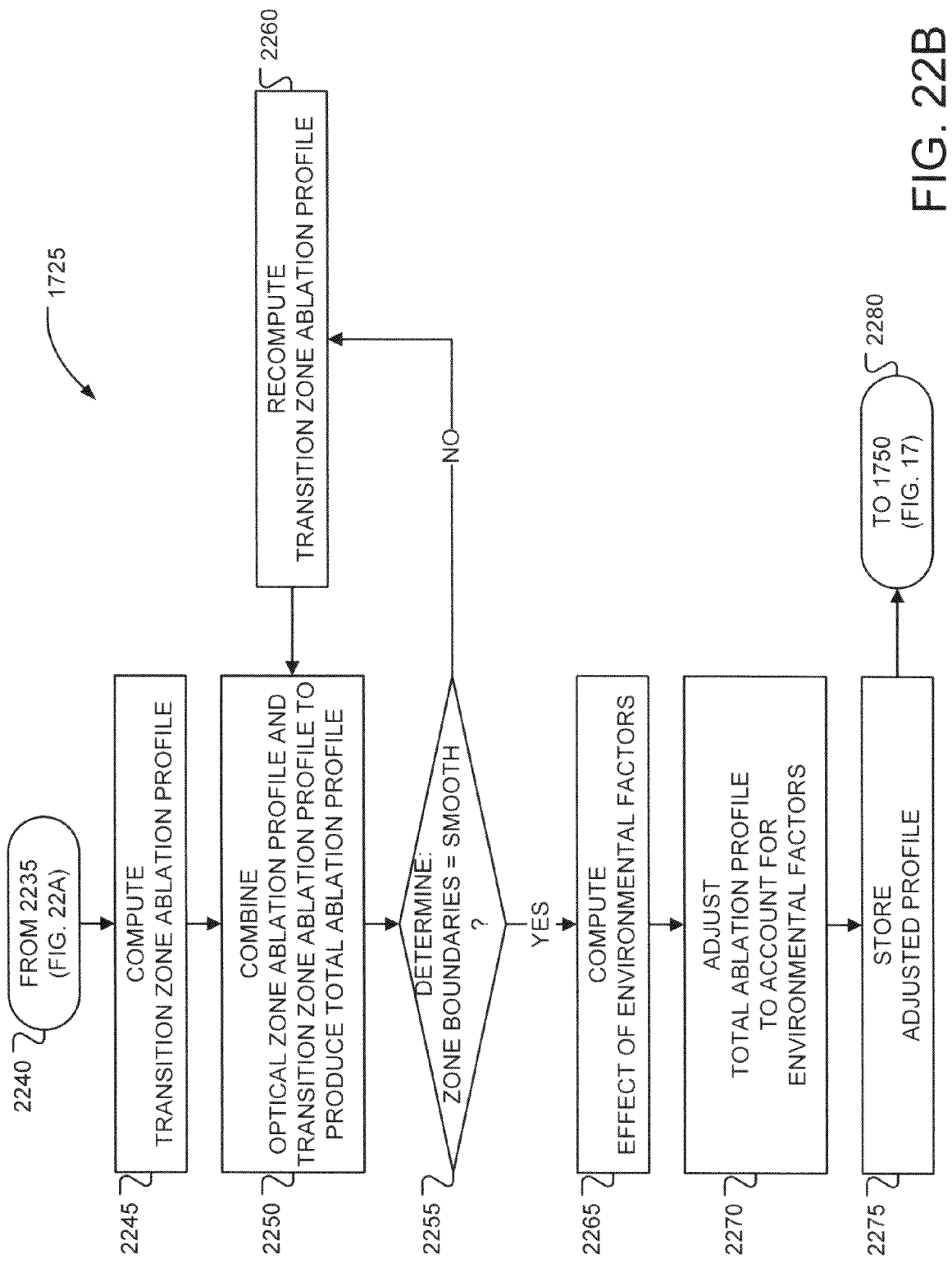

FIGS. 22A and 22B are flowcharts showing, in greater detail, an embodiment of the data-analysis step (1725) from FIG. 17. As shown in FIG. 22A, some embodiments of the data-analysis step (1725) begin when acquired data is retrieved (2210) and a model equation is obtained (2215). The acquired data represents the neuro-ocular waveform, while the model equation represents, for some embodiments, a Zernike polynomial. For other embodiments, the model equation is an expansion of the Zernike polynomial, similar to that shown in Eq. 33. Upon acquiring (2210) the data and obtaining (2215) the model equation, the tilt terms of the Zernike polynomial are set (2220) to zero, as shown with reference to Eqs. 44 and 45. Thereafter, the sphero-cylinder terms are adjusted (2225) in accordance with Eqs. 34 through 36. Once the sphero-cylinder terms have been adjusted (2225), an optical zone ablation profile is computed (2230). For some embodiments, this is done in accordance with Eq. 46. The process continues to FIG. 22B.

As shown in FIG. 22B, in addition to computing (2230) the optical zone ablation profile, the process further computes (2245) a transition zone ablation profile. For some embodiments, the transition zone ablation profile is computed (2245) in accordance with Eq. 47. The optical zone ablation profile and the transition zone ablation profile are then combined (2250) to produce a total ablation profile. Upon producing the total ablation profile, the process determines (2255) whether or not the boundary between the two zones is smooth. If the boundary is not smooth, then the transition zone ablation profile is recomputed (2260), and that transition zone ablation profile is combined (2250) with the optical zone ablation profile. When the boundary between the two zones is smooth, the effect of environmental factors is computed (2265). For some embodiments, the effect of those factors can be represented by Eqs. 49 through 63. The total ablation profile is then adjusted (2270) to correct for those factors. That ablation profile is then stored (2275). In some embodiments, the profile is stored (2275) locally while, in other embodiments, the profile is stored (2275) at a remote repository. As shown in the embodiment of FIGS. 22A and 22B, such a process provides a different approach to vision correction.

Figure 23:
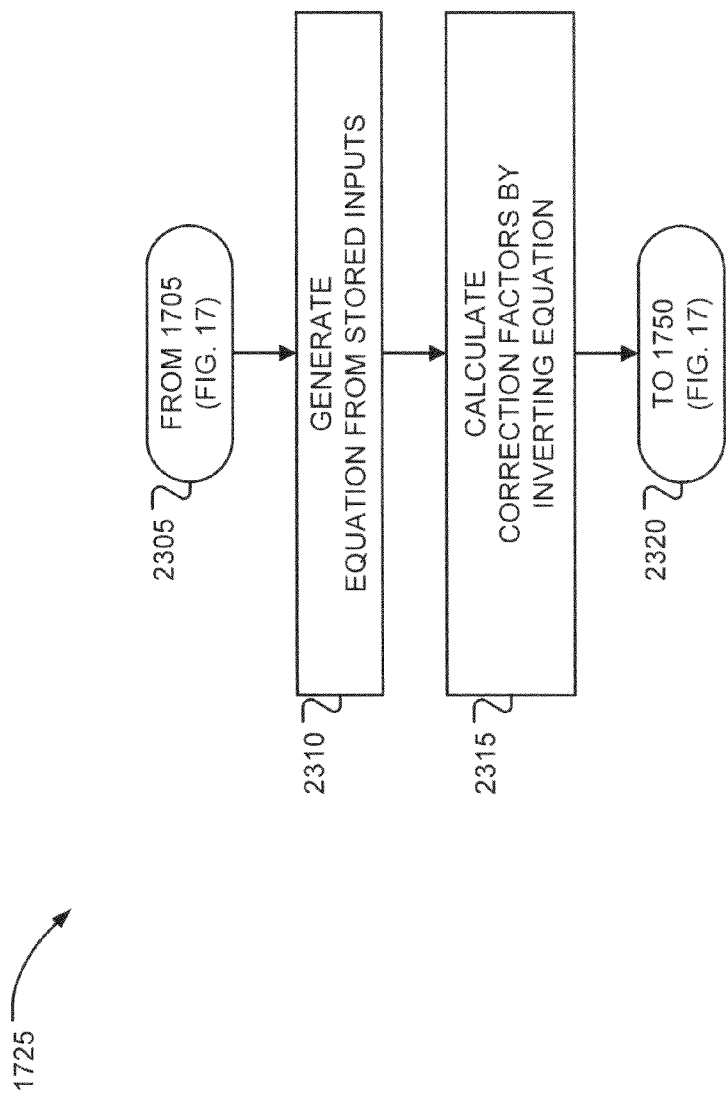
FIG. 23 is a flowchart showing, in greater detail, another embodiment of the data-analysis step from FIG. 17.

FIG. 23 is a flowchart showing, in greater detail, another embodiment of the data-analysis step (1725) from FIG. 17. As shown in FIG. 23, for some embodiments, the data-analysis step (1725) can be seen as a two-step process in which an equation is generated (2310) from the stored inputs, and correction factors are calculated (2315) by inverting the equation. In some embodiments, the process of FIG. 23 can be seen as the computation of the coefficients in accordance with one or more of Eqs. 1 through 38.

Figure 24:
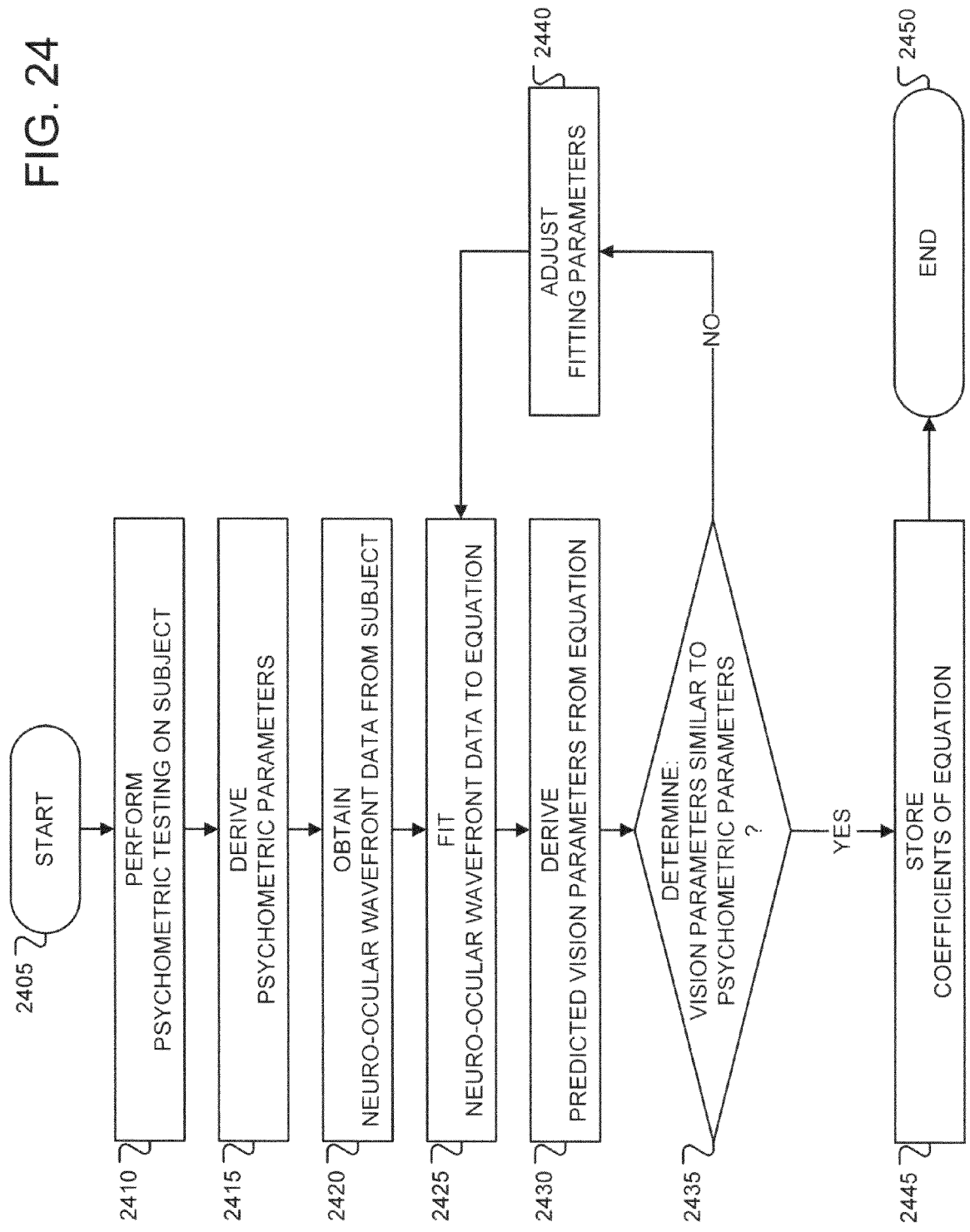
FIG. 24 is a flowchart showing another embodiment of a method for acquiring and processing neuro-ocular wavefront data.

FIG. 24 is a flowchart showing another embodiment of a method for acquiring and processing neuro-ocular wavefront data. As shown in FIG. 24, for some embodiments, the process begins with psychometric testing being performed (2410) on a subject (or patient). Since various psychometric testing is known in the field, further discussion of psychometric testing is omitted here. Upon performing (2410) the psychometric tests, psychometric parameters are derived (2415). In addition to performing psychometric tests, neuro-ocular wavefront data is obtained (2420) from the subject. That neuro-ocular wavefront data is fit (2425) to an equation. For some embodiments, the equation is a Zernike polynomial that represents a neuro-ocular wavefront. From the equation, various predicted vision parameters are derived (2430). Upon deriving (2430) the predicted vision parameters, the process determines (2435) whether or not the vision parameters are similar to the psychometric parameters. If there is a substantial discrepancy between the vision parameters and the psychometric parameters, then the fitting parameters for the equation are adjusted (2440) and the neuro-ocular wavefront data is fit (2425) using the adjusted parameters. If the vision parameters and the psychometric parameters are in substantial agreement, then the coefficients of the equation are stored (2445).

Figure 25:
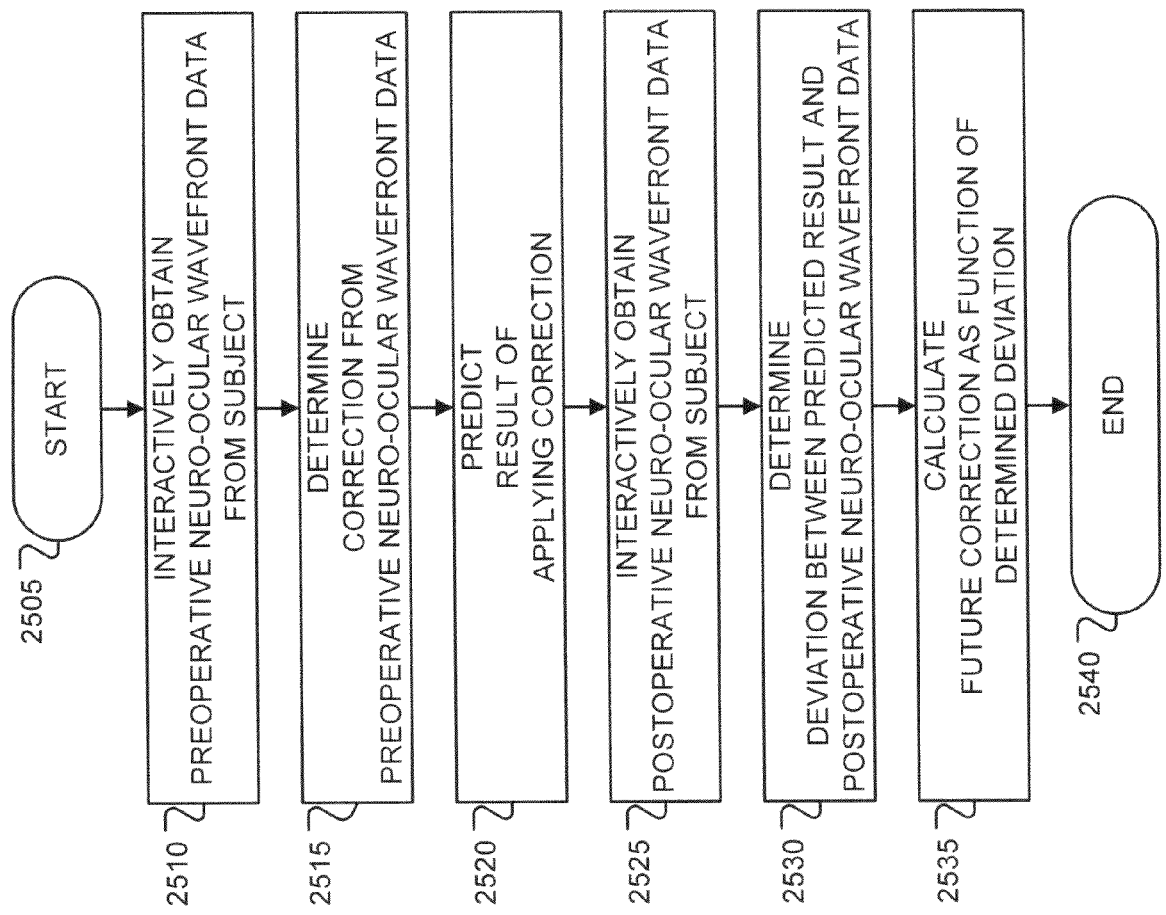
FIG. 25 is a flowchart showing an embodiment of a method for acquiring and processing neuro-ocular wavefront data, in which the processing of subsequently-acquired data is refined.

FIG. 25 is a flowchart showing an embodiment of a method for acquiring and processing neuro-ocular wavefront data, in which the processing of subsequently-acquired data is refined. As such, the embodiment of FIG. 25 can be seen as a process in which preoperative neuro-ocular wavefront data is interactively obtained (2510) from a subject. From the preoperative neuro-ocular wavefront data, a correction is determined (2515), and a result of applying the correction is predicted (2520). Once the subject has been treated, in accordance with one or more available treatments, as outlined above, postoperative neuro-ocular wavefront data is interactively obtained (2525) from the subject. Thereafter, the deviation between the preoperative neuro-ocular wavefront data and the postoperative neuro-ocular wavefront data is determined (2530). From the determined deviation, future corrections are calculated (2535). As seen from the embodiment of FIG. 25, by having both postoperative and preoperative neuro-ocular wavefront data, future treatments can be refined.

FIG. 26 is a flowchart showing an embodiment of a method for acquiring and processing neuro-ocular wavefront data, in which multiple sets of data are statistically analyzed. As shown in FIG. 26, multiple sets of neuro-ocular wavefront data are interactively obtained (2620). For some embodiments, the multiple sets of data can be obtained from multiple clinical sites, such as those shown in FIG. 16. The interactively-obtained neuro-ocular wavefront data is then stored (2630). For some embodiments, the data is stored locally, while, for other embodiments, the data is stored remotely. Thereafter, the stored neuro-ocular wavefront data is statistically analyzed (2640). For some embodiments, the statistical analysis can be seen as a two-step process having the steps of applying (2650) a statistical regression across the multiple sets of neuro-ocular wavefront data, and determining (2660) parameters of a fitting algorithm using the results of the statistical regression. The fitting algorithm can be a least squares fit of the coefficients of a Zernike polynomial, as described above. As previously noted, the aggregation of multiple sets of data provides an approach to refining treatment methods, insofar as effect from similar treatments can be signal averaged over the multiple sets of data.

Figure 27B:
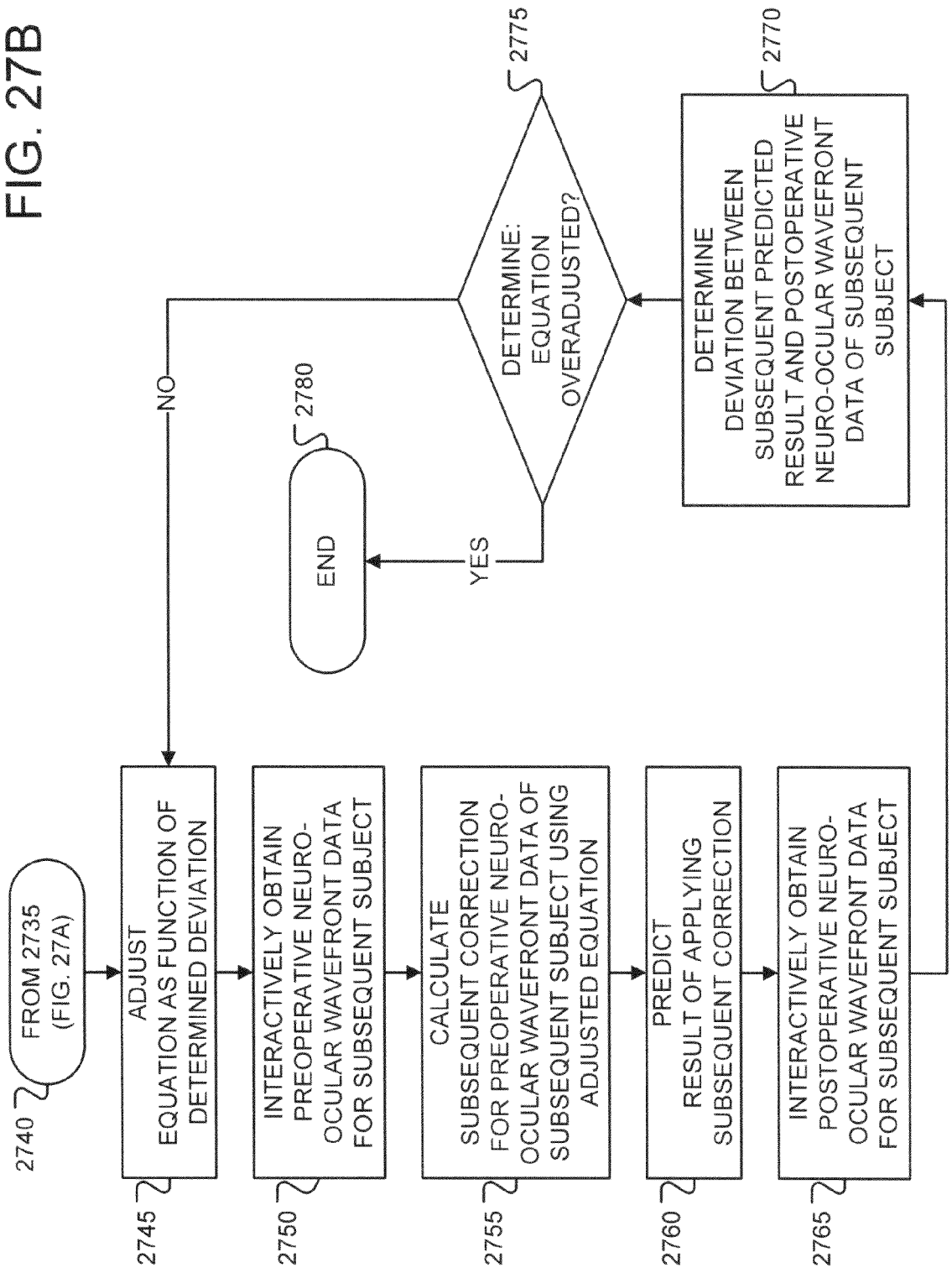

FIGS. 27A and 27B are flowcharts showing another embodiment of a method for acquiring and processing neuro-ocular wavefront data, in which multiple sets of data are statistically analyzed. In this embodiment, the process begins with the interactive obtaining (2710) of preoperative neuro-ocular wavefront data from an initial subject. Thereafter, an initial correction is calculated (2715) from the preoperative neuro-ocular wavefront data of the initial subject. Also, an initial result of applying that correction is predicted (2720). This can be done in accordance with one or more of the above-identified Eqs. 1 through 75. Once the initial subject has been treated, in accordance with one or more of the above-identified treatments, postoperative neuro-ocular wavefront data is interactively obtained (2725) from the initial subject. Subsequently, a deviation between the postoperative neuro-ocular wavefront data and the preoperative neuro-ocular wavefront data is determined (2730) for the initial subject. The process continues to FIG. 27B, where the various coefficients of the corresponding equations are adjusted (2745) as a function of the determined deviation. It should be appreciated that the coefficients are adjusted as needed. Thus, for some embodiments, only a subset of the coefficients are adjusted to account for substantial deviations from the predicted values.

The process of FIG. 27B continues by interactively obtaining (2750) preoperative neuro-ocular wavefront data for a subsequent subject. Thereafter, a correction is calculated (2755) for that subject using the adjusted equation. The process then predicts (2760) a result of applying that calculated (2755) correction. Once the subsequent subject has been treated, postoperative neuro-ocular wavefront data is interactively obtained (2765) from that subject, and the deviation between the predicted result and the postoperative neuro-ocular wavefront data for that subject is determined (2770). From that determined (2770) deviation, the process further determines (2775) whether or not the adjustment to the equation was appropriate. If the adjustment is determined to be appropriate, then the process ends, and the derivation of the coefficients for the equation has been sufficiently refined. Alternatively, if the adjustment is determined to be insufficient or too extreme, then the process recursively readjusts the coefficients of the equation until an appropriate adjustment has been made.

As shown with reference to FIGS. 1 through 31, visual aberrometry is an improvement to both visual acuity and ocular aberrometry, insofar as visual aberrometry uses neuro-ocular wavefront data. As such, visual aberrometry determines the patient preferred retinal plane and takes into account the neurological pathways by combining subject feedback with the physio-optical characteristics of the eye. The aggregate effect of the neurological pathway, in combination with the characteristics of the eye, provides more accurate information for vision diagnosis, vision treatment, or a combination of both.

The processor, and the components that perform the various functions of the processor, may be implemented in hardware, software, firmware, or a combination thereof. In the preferred embodiment(s), the processor and its functional components are implemented in software or firmware that is stored in a memory and that is executed by a suitable instruction execution system. If implemented in hardware, as in an alternative embodiment, the processor and its functional components can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Any process descriptions or blocks in flow charts should be understood as representing modules, segments, or portions of code which include one or more executable instructions for implementing specific logical functions or steps in the process, and alternate implementations are included within the scope of the preferred embodiment of the present invention in which functions may be executed out of order from that shown or discussed, including substantially concurrently or in reverse order, depending on the functionality involved, as would be understood by those reasonably skilled in the art of the present invention.

The neuro-ocular wavefront program and the statistical regression program, which comprise an ordered listing of executable instructions for implementing logical functions, can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer-readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical). Note that the computer-readable medium could even be paper or another suitable medium upon which the program is printed, as the program can be electronically captured via, for instance, optical scanning of the paper or other medium, then compiled, interpreted or otherwise processed in a suitable manner if necessary, and then stored in a computer memory.

Although exemplary embodiments have been shown and described, it will be clear to those of ordinary skill in the art that a number of changes, modifications, or alterations to the invention as described may be made. All such changes, modifications, and alterations should therefore be seen as within the scope of the disclosure.

The invention claimed is:

1. A system comprising:
a refractometer configured to interactively obtain neuro-ocular wavefront data from a subject, the neuro-ocular wavefront data representing anomalies in a visual system of the subject, the refractometer further being configured to transmit the neuro-ocular wavefront data; and
an information storage device configured to receive the neuro-ocular wavefront data, the information storage device being located remotely from the refractometer.

2. A system comprising:
a computer configured to retrieve neuro-ocular wavefront data from an information storage device, the neuro-ocular wavefront data representing anomalies in a visual system of a subject;
a processor located within the computer, the processor being configured to calculate a correction from the neuro-ocular wavefront data, the corresponding to a treatment for reducing the anomalies in the visual system of the subject.

3. The system of claim 2, the correction corresponding to a prescription for spectacles.

4. The system of claim 2, the correction corresponding to a prescription for a contact lens.

5. The system of claim 2, the correction corresponding to a treatment profile for a refractive surgical technique.

6. The system of claim 5, the refractive surgical technique being one selected from the group consisting of:
radial keratotomy (RK);
astigmatic keratotomy (AK);
automated lamellar keratoplasty (ALK);
photorefractive keratectomy (PRK);
laser in situ keratomileusis (LASIK);
intracorneal ring segments (Intacs);
intracorneal lens surgery;
laser thermal keratoplasty (LTK);
phakic intraocular lenses; and
any combination thereof.

7. A method comprising the steps of:
interactively obtaining preoperative neuro-ocular wavefront data from a subject, the preoperative neuro-ocular wavefront data representing anomalies in the visual system of the subject, the preoperative neuro-ocular wavefront data being represented by a first equation, the first equation having a first set of coefficients;
determining a correction for reducing the anomalies in the visual system of the subject, the correction being a function of the preoperative neuro-ocular wavefront data;
predicting a result of applying the determined correction;
interactively obtaining postoperative neuro-ocular wavefront data for the subject, the postoperative neuro-ocular wavefront data representing a corrected visual system of the subject, the postoperative neuro-ocular wavefront data being represented by a second equation, the second equation having a second set of coefficients; and
determining a deviation between the predicted result and the postoperative neuro-ocular wavefront data.

8. The method of claim 7, further comprising the step of calculating a future correction, the future correction being a function of the determined deviation between the predicted result and the postoperative neuro-ocular wavefront data.

9. The method of claim 7, the correction comprising a prescription for spectacles.

10. The method of claim 7, the correction comprising a prescription for a contact lens.

11. The method of claim 7, the correction comprising a treatment profile for a refractive surgical technique.

12. The method of claim 11, the refractive surgical technique being one selected from the group consisting of:
radial keratotomy (RK);
astigmatic keratotomy (AK);
automated lamellar keratoplasty (ALK);
photorefractive keratectomy (PRK);
laser in situ keratomileusis (LASIK);
intracorneal ring segments (Intacs);
infracornea lens surgery;
laser thermal keratoplasty (LTK);
phakic intraocular lenses; and
any combination thereof.

13. A system comprising:
a refractometer configured to interactively obtain preoperative neuro-ocular wavefront data from a subject, the preoperative neuro-ocular wavefront data representing anomalies in the visual system of the subject, the preoperative neuro-ocular wavefront data being represented by a first equation, the first equation having a first set of coefficients, the refractometer further being configured to interactively obtain postoperative neuro-ocular wavefront data for the subject, the postoperative neuro-ocular wavefront data representing a corrected visual system of the subject, the postoperative neuro-ocular wavefront data being represented by a second equation, the second equation having a second set of coefficients; and a processor configured to determine a correction for reducing the anomalies in the visual system of the subject, the correction being a function of the preoperative neuro-ocular wavefront data, the processor further being configured to predict a result of applying the determined correction, the processor further being configured to determine a deviation between the predicted result and the postoperative neuro-ocular wavefront data.

14. The system of claim 13, the processor being an integrated component of the refractometer.

15. The system of claim 13, the processor being located remotely from the refractometer.

16. The system of claim 13, the processor further being configured to calculate a future correction, the future correction being a function of the determined deviation between the predicted result and the postoperative neuro-ocular wavefront data.

17. The system of claim 13, the correction comprising a prescription for spectacles.

18. The system of claim 13, the correction comprising a prescription for a contact lens.

19. The system of claim 13, the correction comprising a treatment profile for a refractive surgical technique.

20. The system of claim 19, the refractive surgical technique being one selected from the group consisting of:
 radial keratotomy (RK);
 astigmatic keratotomy (AK);
 automated lamellar keratoplasty (ALK);
 photorefractive keratectomy (PRK);
 laser in situ keratomileusis (LASIK);
 intracorneal ring segments (Intacs);
 intracornea lens surgery;
 laser thermal keratoplasty (LTK);
 phakic intraocular lenses; and
 any combination thereof.

21. A system comprising:
 means for interactively obtaining preoperative neuro-ocular wavefront data from a subject, the preoperative neuro-ocular wavefront data representing anomalies in the visual system of the subject, the preoperative neuro-ocular wavefront data being represented by a first equation, the first equation having a first set of coefficients;
 means for determining a correction for reducing the anomalies in the visual system of the subject, the correction being a function of the preoperative neuro-ocular wavefront data;
 means for predicting a result of applying the determined correction;
 means for interactively obtaining postoperative neuro-ocular wavefront data for the subject, the postoperative neuro-ocular wavefront data representing a corrected visual system of the subject, the postoperative neuro-ocular wavefront data being represented by a second equation, the second equation having a second set of coefficients; and
 means for determining a deviation between the predicted result and the postoperative neuro-ocular wavefront data.

22. The method of claim 21, further comprising means for calculating a future correction, the future correction being a function of the determined deviation between the predicted result and the postoperative neuro-ocular wavefront data.

23. A computer-readable medium comprising:
 computer-readable code adapted to instruct a programmable device to interactively obtain preoperative neuro-ocular wavefront data from a subject, the preoperative neuro-ocular wavefront data representing anomalies in the visual system of the subject, the preoperative neuro-ocular wavefront data being represented by a first equation, the first equation having a first set of coefficients;
 computer-readable code adapted to instruct a programmable device to determine a correction for reducing the anomalies in the visual system of the subject, the correction being a function of the preoperative neuro-ocular wavefront data;
 computer-readable code adapted to instruct a programmable device to predict a result of applying the determined correction;
 computer-readable code adapted to instruct a programmable device to interactively obtain postoperative neuro-ocular wavefront data for the subject, the postoperative neuro-ocular wavefront data representing a corrected visual system of the subject, the postoperative neuro-ocular wavefront data being represented by a second equation, the second equation having a second set of coefficients; and
 computer-readable code adapted to instruct a programmable device to determine a deviation between the predicted result and the postoperative neuro-ocular wavefront data.

24. A computer-readable medium as defined in claim 23, further comprising computer-readable code adapted to instruct a programmable device to calculate a future correction, the future correction being a function of the determined deviation between the predicted result and the postoperative neuro-ocular wavefront data.

25. A method comprising the steps of:
 interactively obtaining multiple sets of neuro-ocular wavefront data, each neuro-ocular wavefront data representing anomalies in the visual system of a corresponding subject, the neuro-ocular wavefront data being represented by an equation, the equation having coefficients;
 storing the multiple sets of neuro-ocular wavefront data at a central repository; and
 statistically analyzing the multiple sets of neuro-ocular wavefront data.

26. The method of claim 25, the step of statistically analyzing the multiple sets of neuro-ocular wavefront data comprising the step of applying a statistical regression across the multiple sets of neuro-ocular wavefront data.

27. The method of claim 26, further comprising the step of determining parameters in an algorithm, the algorithm being configured to
 calculate a
correction for anomalies in a visual system of a subject.

28. The method of claim 25, the multiple sets of neuro-ocular wavefront data comprising:
 a first set of preoperative neuro-ocular wavefront data for a first subject, the first set of preoperative neuro-ocular wavefront data representing anomalies in the visual system of the first subject, the first set of preoperative neuro-ocular wavefront data being represented by a first equation, the first equation having a first set of coefficients;

a first set of postoperative neuro-ocular wavefront data for the first subject, the first set of postoperative neuro-ocular wavefront data representing a corrected visual system of the first subject, the visual system of the first subject being corrected by a first treatment, the postoperative neuro-ocular wavefront data being represented by a second equation, the second equation having a second set of coefficients;

a second set of preoperative neuro-ocular wavefront data for a second subject, the second set of preoperative neuro-ocular wavefront data representing anomalies in the visual system of the second subject, the anomalies in the visual system of the second subject being substantially similar to the anomalies in the visual system of the first subject, the second set of preoperative neuro-ocular wavefront data being represented by a third equation, the third equation having a third set of coefficients; and a second set of postoperative neuro-ocular wavefront data for the second subject, the second set of postoperative neuro-ocular wavefront data representing a corrected visual system of the second subject, the visual system of the second subject being corrected by a second treatment, the second treatment being substantially different from the first treatment, the postoperative neuro-ocular wavefront data being represented by a fourth equation, the fourth equation having a fourth set of coefficients.

29. The method of claim 28, the first treatment being one selected from the group consisting of:
   a prescription for spectacles;
   a prescription for a contact lens;
   radial keratotomy (RK);
   astigmatic keratotomy (AK);
   automated lamellar keratoplasty (ALK);
   photorefractive keratectomy (PRK);
   laser in situ keratomileusis (LASIK);
   intracorneal ring segments (Intacs);
   infracornea lens surgery;
   laser thermal keratoplasty (LTK);
   phakic intraocular lenses; and
   any combination thereof.

30. The method of claim 28, the second treatment being one selected from the group consisting of:
   a prescription for spectacles;
   a prescription for a contact lens;
   radial keratotomy (RK);
   astigmatic keratotomy (AK);
   automated lamellar keratoplasty (ALK);
   photorefractive keratectomy (PRK);
   laser in situ keratomileusis (LASIK);
   intracorneal ring segments (Intacs);
   infracornea lens surgery;
   laser thermal keratoplasty (LTK);
   phakic intraocular lenses; and
   any combination thereof.

31. The method of claim 25, the multiple sets of neuro-ocular wavefront data comprising:
   a first set of preoperative neuro-ocular wavefront data for a first subject, the first set of preoperative neuro-ocular wavefront data representing anomalies in the visual system of the first subject, the first set of preoperative neuro-ocular wavefront data being represented by a first equation, the first equation having a first set of coefficients;
   a first set of postoperative neuro-ocular wavefront data for the first subject, the first set of postoperative neuro-ocular wavefront data representing a corrected visual system of the first subject, the visual system of the first subject being corrected by a first treatment, the postoperative neuro-ocular wavefront data being represented by a second equation, the second equation having a second set of coefficients;
   a second set of preoperative neuro-ocular wavefront data for a second subject, the second set of preoperative neuro-ocular wavefront data representing anomalies in the visual system of the second subject, the anomalies in the visual system of the second subject being substantially similar to the anomalies in the visual system of the first subject, the second set of preoperative neuro-ocular wavefront data being represented by a third equation, the third equation having a third set of coefficients; and
   a second set of postoperative neuro-ocular wavefront data for the second subject, the second set of postoperative neuro-ocular wavefront data representing a corrected visual system of the second subject, the visual system of the second subject being corrected by a second treatment, the second treatment being substantially similar to the first treatment, the postoperative neuro-ocular wavefront data being represented by a fourth equation, the fourth equation having a fourth set of coefficients.

32. The method of claim 31, the first treatment being one selected from the group consisting of:
   a prescription for spectacles;
   a prescription for a contact lens;
   radial keratotomy (RK);
   astigmatic keratotomy (AK);
   automated lamellar keratoplasty (ALK);
   photorefractive keratectomy (PRK);
   laser in situ keratomileusis (LASIK);
   intracorneal ring segments (Intacs);
   intracornea lens surgery;
   laser thermal keratoplasty (LTK);
   phakic Intraocular lenses; and
   any combination thereof.

33. The method of claim 31, the second treatment being one selected from the group consisting of:
   prescription for spectacles;
   a prescription for a contact lens;
   radial keratotomy (RK);
   astigmatic keratotomy (AK);
   automated lamellar keratoplasty (ALK);
   photorefractive keratectomy (PRK);
   laser in situ keratomileusis (LASIK);
   intracorneal ring segments (Intacs);
   intracornea lens surgery;
   laser thermal keratoplasty (LTK);
   phakic intraocular lenses; and
   any combination thereof.

34. The method of claim 25, the multiple sets of neuro-ocular wavefront data comprising:
   a first set of preoperative neuro-ocular wavefront data for a first subject, the first set of preoperative neuro-ocular wavefront date representing anomalies in the visual system of the first subject, the first set of preoperative neuro-ocular wavefront data being represented by a first equation, the first equation having a first set of coefficients;
   a first set of postoperative neuro-ocular wavefront data for the first subject, the first set of postoperative neuro-ocular wavefront data representing a corrected visual system of the first subject, the postoperative neuro-ocular wavefront data being represented by a second equation, the second equation having a second set of coefficients;

a second set of preoperative neuro-ocular wavefront data for a second subject, the second set of preoperative neuro-ocular wavefront data representing anomalies in the visual system of the second subject, the second set of preoperative neuro-ocular wavefront data being represented by a third equation, the third equation having a third set of coefficients; and a second set of postoperative neuro-ocular wavefront data for the second subject, the second set of postoperative neuro-ocular wavefront data representing a corrected visual system of the second subject, the postoperative neuro-ocular wavefront data being represented by a fourth equation, the fourth equation having a fourth set of coefficients.

35. The method of claim 34, the step of statistically analyzing the multiple sets of neuro-ocular wavefront data comprising the steps of:

determining a first correction for reducing the anomalies in the visual system of the first subject, the first correction being a function of the first preoperative neuro-ocular wavefront data;

predicting a first result of applying the first correction;

determining a first deviation between the predicted first result and the first set of postoperative neuro-ocular wavefront data;

determining a second correction for reducing the anomalies in the visual system of the second subject, the second correction being a function of the second preoperative neuro-ocular wavefront data;

predicting a second result of applying the second correction; and determining a second deviation between the predicted second result and the second set of postoperative neuro-ocular wavefront data; and comparing the first deviation with the second deviation.

36. The method of claim 35, the step of determining the first deviation comprising the step of identifying a mismatch between the first equation and the second equation, the step of determining the second deviation comprising the step of identifying a mismatch between the third equation and the fourth equation.

37. The method of claim 36, each of the equations representing a vision parameter, the vision parameter being selected from the group consisting of:

photopic pupil diameter;
mesopic pupil diameter,
cycloplegic pupil diameter;
near-vision preoperative refraction sphere;
near-vision preoperative refraction cylinder;
near-vision preoperative refraction axis;
far-vision preoperative refraction sphere;
far-vision preoperative refraction cylinder,
far-vision preoperative refraction axis;
near-vision postoperative refraction sphere;
near-vision postoperative refraction cylinder;
near-vision postoperative refraction axis;
far-vision postoperative refraction sphere;
far-vision postoperative refraction cylinder,
far-vision postoperative refraction axis;
left eye;
right eye;
asphericity;
axis angle;
optical zone diameter;
transition zone diameter;
central pachymetry;
spherical aberration as a percent of total root-mean-square (RMS) aberration;
coma as a percent of total RMS aberration;
trefoil as a percent of total RMS aberration;
high-order aberrations as a percent of total RMS aberration;
astigmatism index;
corneal width;
front surface corneal curvature;
back surface corneal curvature;
front-to-back alignment
age;
side of dominant eye;
preference between day vision and night vision;
treatment purpose;
ethnicity;
iris color;
gender,
temperature;
humidity;
microkeratome used for corneal resection;
flap size;
time elapsed from opening of flap to ablation;
surgeon;
estimated total time during opening of flap;
expected flap thickness;
procedure type;
scanner used;
laser used;
day of surgery;
location of flap hinge; and
any combination thereof.

38. A system comprising:

a refractometer configured to interactively obtain multiple sets of neuro-ocular wavefront data, each neuro-ocular wavefront data representing anomalies in the visual system of a corresponding subject, the neuro-ocular wavefront data being represented by an equation, the equation having coefficients;

an information storage device configured to store the multiple sets of neuro-ocular wavefront data at a central repository; and a processor configured to statistically analyzing the multiple sets of neuro-ocular wavefront data.

39. The system of claim 38, the processor being integrated with the refractometer.

40. The system of claim 38, the processor being located remotely from the refractometer.

41. The system of claim 38, the information storage device being integrated with the refractometer.

42. The system of claim 38, the information storage device being located remotely from the refractometer.

43. The system of claim 38, the processor further being configured to apply a statistical regression across the multiple sets of neuro-ocular wavefront data, the processor further being configured to determine parameters in an algorithm, the algorithm being configured to calculate a correction for anomalies in a visual system of a subject.

44. The system of claim 38, the multiple sets of neuro-ocular wavefront data comprising:

a first set of preoperative neuro-ocular wavefront data for a first subject, the first set of preoperative neuro-ocular wavefront data representing anomalies in the visual system of the first subject, the first set of preoperative neuro-ocular wavefront data being represented by a first equation, the first equation having a first set of coefficients;

a first set of postoperative neuro-ocular wavefront data for the first subject, the first set of postoperative neuro-ocular wavefront data representing a corrected visual system of the first subject, the visual system of the first subject being corrected by a first treatment, the postoperative neuro-ocular wavefront data being represented by a second equation, the second equation having a second set of coefficients;

a second set of preoperative neuro-ocular wavefront data for a second subject, the second set of preoperative neuro-ocular wavefront data representing anomalies in the visual system of the second subject, the anomalies in the visual system of the second subject being substantially similar to the anomalies in the visual system of the first subject, the second set of preoperative neuro-ocular wavefront data being represented by a third equation, the third equation having a third set of coefficients; and a second set of postoperative neuro-ocular wavefront data for the second subject, the second set of postoperative neuro-ocular wavefront data representing a corrected visual system of the second subject, the visual system of the second subject being corrected by a second treatment, the second treatment being substantially different from the first treatment, the postoperative neuro-ocular wavefront data being represented by a fourth equation, the fourth equation having a fourth set of coefficients.

45. The system of claim 38, the multiple sets of neuro-ocular wavefront data comprising:

a first set of preoperative neuro-ocular wavefront data for a first subject, the first set of preoperative neuro-ocular wavefront data representing anomalies in the visual system of the first subject, the first set of preoperative neuro-ocular wavefront data being represented by a first equation, the first equation having a first set of coefficients;

a first set of postoperative neuro-ocular wavefront data for the first subject, the first set of postoperative neuro-ocular wavefront data representing a corrected visual system of the first subject, the visual system of the first subject being corrected by a first treatment, the postoperative neuro-ocular wavefront data being represented by a second equation, the second equation having a second set of coefficients;

a second set of preoperative neuro-ocular wavefront data for a second subject, the second set of preoperative neuro-ocular wavefront data representing anomalies in the visual system of the second subject, the anomalies in the visual system of the second subject being substantially similar to the anomalies in the visual system of the first subject, the second set of preoperative neuro-ocular wavefront data being represented by a third equation, the third equation having a third set of coefficients; and a second set of postoperative neuro-ocular wavefront data for the second subject, the second set of postoperative neuro-ocular wavefront data representing a corrected visual system of the second subject, the visual system of the second subject being corrected by a second treatment, the second treatment being substantially similar to the first treatment, the postoperative neuro-ocular wavefront data being represented by a fourth equation, the fourth equation having a fourth set of coefficients.

46. The system of claim 38, the multiple sets of neuro-ocular wavefront data comprising:

a first set of preoperative neuro-ocular wavefront data for a first subject, the first set of preoperative neuro-ocular wavefront data representing anomalies in the visual system of the first subject, the first set of preoperative neuro-ocular wavefront data being represented by a first equation, the first equation having a fast set of coefficients;

a first set of postoperative neuro-ocular wavefront data for the first subject, the first set of postoperative neuro-ocular wavefront data representing a corrected visual system of the first subject, the postoperative neuro-ocular wavefront data being represented by a second equation, the second equation having a second set of coefficients;

a second set of preoperative neuro-ocular wavefront data for a second subject, the second set of preoperative neuro-ocular wavefront data representing anomalies in the visual system of the second subject, the second set of preoperative neuro-ocular wavefront data being represented by a third equation, the third equation having a third set of coefficients; and a second set of postoperative neuro-ocular wavefront data for the second subject, the second set of postoperative neuro-ocular wavefront data representing a corrected visual system of the second subject, the postoperative neuro-ocular wavefront data being represented by a fourth equation, the fourth equation having a fourth set of coefficients.

47. The system of claim 46, the processor further being configured to determine a first correction for reducing the anomalies in the visual system of the first subject, the first correction being a function of the first preoperative neuro-ocular wavefront data, the processor further being configured to predict a first result of applying the first correction, the processor further being configured to determine a first deviation between the predicted first result and the first set of postoperative neuro-ocular wavefront data, the processor further being configured to determine a second correction for reducing the anomalies in the visual system of the second subject, the second correction being a function of the second preoperative neuro-ocular wavefront data, the processor further being configured to predict a second result of applying the second correction, the processor further being configured to determine a second deviation between the predicted second result and the second set of postoperative neuro-ocular wavefront date, the processor further being configured to compare the first deviation with the second deviation.

48. The system of claim 47, the processor further being configured to identify a mismatch between the first equation and the second equation, processor further being configured to identify a mismatch between the third equation and the fourth equation.

49. A system comprising:

means for interactively obtaining multiple sets of neuro-ocular wavefront data, each neuro-ocular wavefront data representing anomalies to the visual system of a corresponding subject, the neuro-ocular wavefront data being represented by an equation, the equation having coefficients;

means for storing the multiple sets of neuro-ocular wavefront data of a central repository; and means for statistically analyzing the multiple sets of neuro-ocular wavefront data.

50. A computer-readable medium comprising:

computer-readable code adapted to instruct a programmable device to interactively obtain multiple sets of neuro-ocular wavefront data, each neuro-ocular wavefront data representing anomalies in the visual system of a corresponding subject, the neuro-ocular wavefront data being represented by an equation, the equation having coefficients;

computer-readable code adapted to instruct a programmable device to store the multiple sets of neuro-ocular wavefront data at a centre repository; and computer-readable code adapted to instruct a programmable device to statistically analyze the multiple sets of neuro-ocular wavefront data.

51. A method comprising the steps of obtaining neuro-ocular wavefront data; and ascertaining characteristics of a visual system from the obtained neuro-ocular wavefront data.

52. The method of claim 51, further comprising the step of correlating the characteristics of the visual system with vision parameters.

53. A system comprising:

means for obtaining neuro-ocular wavefront data; and means for ascertaining characteristics of a visual system from the obtained neuro-ocular wavefront data.

54. The system of claim 53, further comprising means for correlating the characteristics of the visual system with vision parameters.

55. A system comprising:

a refractometer configured to obtain neuro-ocular wavefront data; and a processor configured to ascertain characteristics of a visual system from the obtained neuro-ocular wavefront data.

56. The system of claim 55, the processor further being configured to correlate the characteristics of the visual system with vision parameters.

57. A computer-readable medium comprising:

computer-readable code adapted to instruct a programmable device to obtain neuro-ocular wavefront data; and computer-readable code adapted to instruct a programmable device to ascertain characteristics of a visual computer-readable medium from the obtained neuro-ocular wavefront data.

58. The computer-readable medium of claim 57, further comprising computer-readable code adapted to instruct a programmable device to correlate the characteristics of the visual system with vision parameters.

* * * * *